US010556707B2

(12) United States Patent
Taylor et al.

(10) Patent No.: US 10,556,707 B2
(45) Date of Patent: Feb. 11, 2020

(54) MODULAR INTERFACE FOR AN AERIAL DRONE

(71) Applicants: Joshua D. Taylor, Fredericksburg, VA (US); Jonathan U. Crook, King George, VA (US); John W. Gawalt, King George, VA (US); Jordan C. Lieberman, Fredericksburg, VA (US); Jessica L. Hildebrand, Fredericksburg, VA (US); Charles T. Miller, Fredericksburg, VA (US); Troy S. Newhart, King George, VA (US)

(72) Inventors: Joshua D. Taylor, Fredericksburg, VA (US); Jonathan U. Crook, King George, VA (US); John W. Gawalt, King George, VA (US); Jordan C. Lieberman, Fredericksburg, VA (US); Jessica L. Hildebrand, Fredericksburg, VA (US); Charles T. Miller, Fredericksburg, VA (US); Troy S. Newhart, King George, VA (US)

(73) Assignee: United States of America, as represented by the Secretary of the Navy, Arlington, VA (US)

( * ) Notice: Subject to any disclaimer, the term of this patent is extended or adjusted under 35 U.S.C. 154(b) by 262 days.

(21) Appl. No.: 15/813,315

(22) Filed: Nov. 15, 2017

(65) Prior Publication Data

US 2018/0362184 A1 Dec. 20, 2018

Related U.S. Application Data

(60) Provisional application No. 62/519,258, filed on Jun. 14, 2017.

(51) Int. Cl.
*B64D 47/08* (2006.01)
*B64C 39/02* (2006.01)
*G01N 33/00* (2006.01)

(52) U.S. Cl.
CPC ............ *B64D 47/08* (2013.01); *B64C 39/024* (2013.01); *G01N 33/0055* (2013.01); *G01N 33/0057* (2013.01); *G01N 33/0062* (2013.01); *B64C 2201/126* (2013.01); *B64C 2201/127* (2013.01)

(58) Field of Classification Search
CPC .......... B64C 2201/126; G01N 33/0055; G01N 33/0057; G01N 33/0062
USPC ........................................................ 73/866.5
See application file for complete search history.

(56) References Cited

U.S. PATENT DOCUMENTS

| 6,840,480 B2 * | 1/2005 | Carroll .................. B64C 39/024 244/117 R |
| 7,073,748 B2 * | 7/2006 | Maurer .................. B64C 39/024 209/143 |
| 2012/0035787 A1 * | 2/2012 | Dunkelberger ....... B64C 39/024 701/3 |

(Continued)

*Primary Examiner* — Daniel S Larkin
(74) *Attorney, Agent, or Firm* — Gerhard W. Thielman

(57) ABSTRACT

A modular sensor platform is provided for installation on an unmanned aerial vehicle (UAV) for sensor operation. The platform includes an external shell that defines an internal volume, an interface module, and a mission module. The shell inserts between sections of the UAV. The interface module attaches to the shell within the volume. The mission module attaches to the shell within the volume. The interface module includes a communications package, a battery package and an air intake.

5 Claims, 20 Drawing Sheets

(56) References Cited

U.S. PATENT DOCUMENTS

2018/0072415 A1\* 3/2018 Cantrell ............... G05D 1/0027

\* cited by examiner

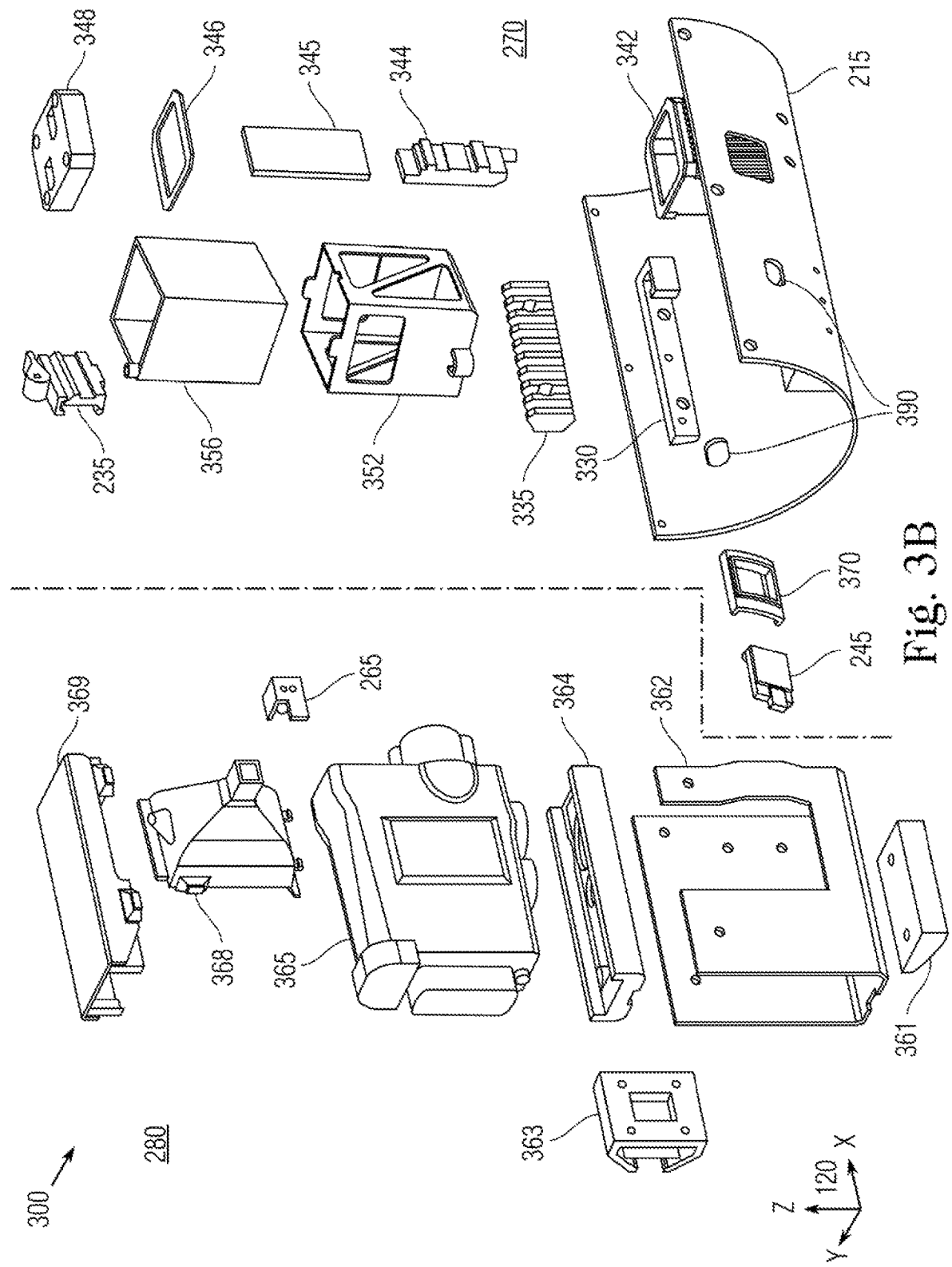

US 10,556,707 B2

MODULAR INTERFACE FOR AN AERIAL DRONE

CROSS REFERENCE TO RELATED APPLICATION

Pursuant to 35 U.S.C. § 119, the benefit of priority from provisional application 62/519,258, with a filing date of Jun. 14, 2017, is claimed for this non-provisional application.

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to modular interface housings and components for incorporation into aerial drones. In particular, the invention relates to integration of particulate sensors of pathogenic airborne materials for remote detection aboard unmanned aircraft.

The unmanned aerial vehicle (UAV) concept has been employed for several decades for reconnaissance to reduce cost and risk in comparison to piloted aircraft. The ScanEagle aerial drone by Insitu (a subsidiary of Boeing) represents a modular UAV designed for low-flying reconnaissance and operates world-wide. Such UAV platforms constitute the sortie portion of unmanned aerial systems (UAS). The Scan Eagle is launched by catapult and recovered by snag wires. Introduced in 2005, the ScanEagle has a wingspan of just over ten feet and a top speed of 92 miles-per-hour (mph).

FIG. 1 shows a perspective assembly view 100 of a ScanEagle drone 110. A compass rose 120 in Cartesian coordinates shows x, y and z orthogonal axes for respective forward-longitudinal, port-lateral and azimuth directions. A segment edge interface 130 joins the nose cone with the fuselage, between which a sensor package can be inserted.

SUMMARY

Conventional sensor packages on aerial drones yield disadvantages addressed by various exemplary embodiments of the present invention. In particular, various exemplary embodiments provide a modular sensor platform for installation on an unmanned aerial vehicle (UAV) for sensor operation. The platform includes an external shell that defines an internal volume, an interface module, and a mission module. The shell inserts between sections of the UAV. The interface module attaches to the shell within the volume. The mission module attaches to the shell within the volume. The interface module includes a communications package, a battery package and an air intake.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which:

FIGS. 3A, 3B, 3C and 3D are isometric exploded views of components for an interface section and a chemical mission module;

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

The Sly Fox program at Naval Surface Warfare Center-Dahlgren Division (NSWCDD) is a workforce development initiative that engages a team of early career scientists and engineers to rapidly prototype a system to meet a specific need in the Department of Defense (DoD) with a limited amount of time and a strict budget. Sly Fox Mission 21 was tasked with developing a system that is compatible with various UAS platforms that supports a suite of chemical, biological, or radiological (CBR) detection and collection capabilities, and is able to relay threat data to a ground control station (GCS).

The Sly Fox team developed the Senses CBR Agents Pre-Engagement & Goes Over All Terrain (SCAPEGOAT) system to satisfy these criteria. The SCAPEGOAT system was built on a relatively small budget and timeline, and was designed to leverage many previously built CBR technologies, especially sensors. To test and evaluate the system, flights aboard ScanEagle and DJI S1000 Unmanned Aerial Systems were conducted at NSWCDD.

The system comprises a common interface onto which either a chemical, biological, or radiological mission module can be installed. The system is platform agnostic, and is capable of being deployed on sundry unmanned aerial systems, with possible expansion into unmanned ground and unmanned surface systems, as well as on the exteriors of manned vehicles. The system is a multi-mission, multi-platform toolkit for CBR collection and/or detection.

Figure 1:
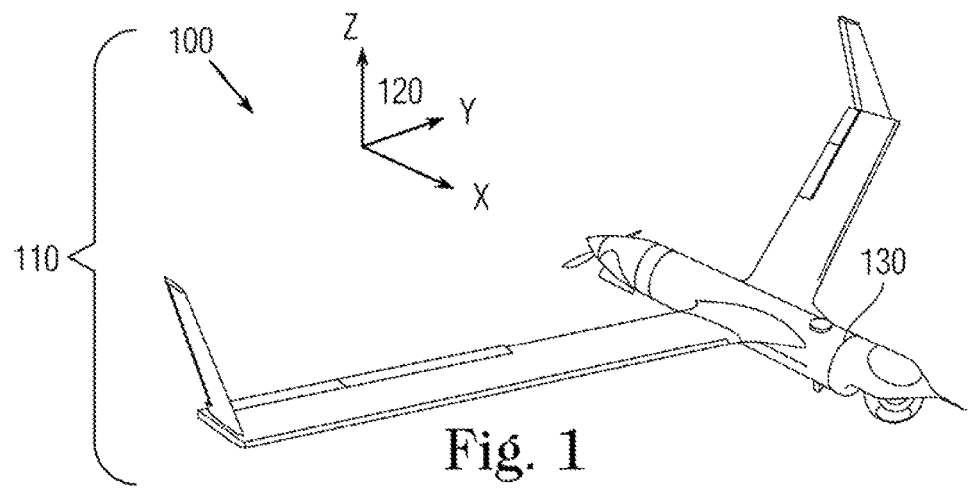
FIG. 1 is a perspective view of a ScanEagle drone.
Figure 2:
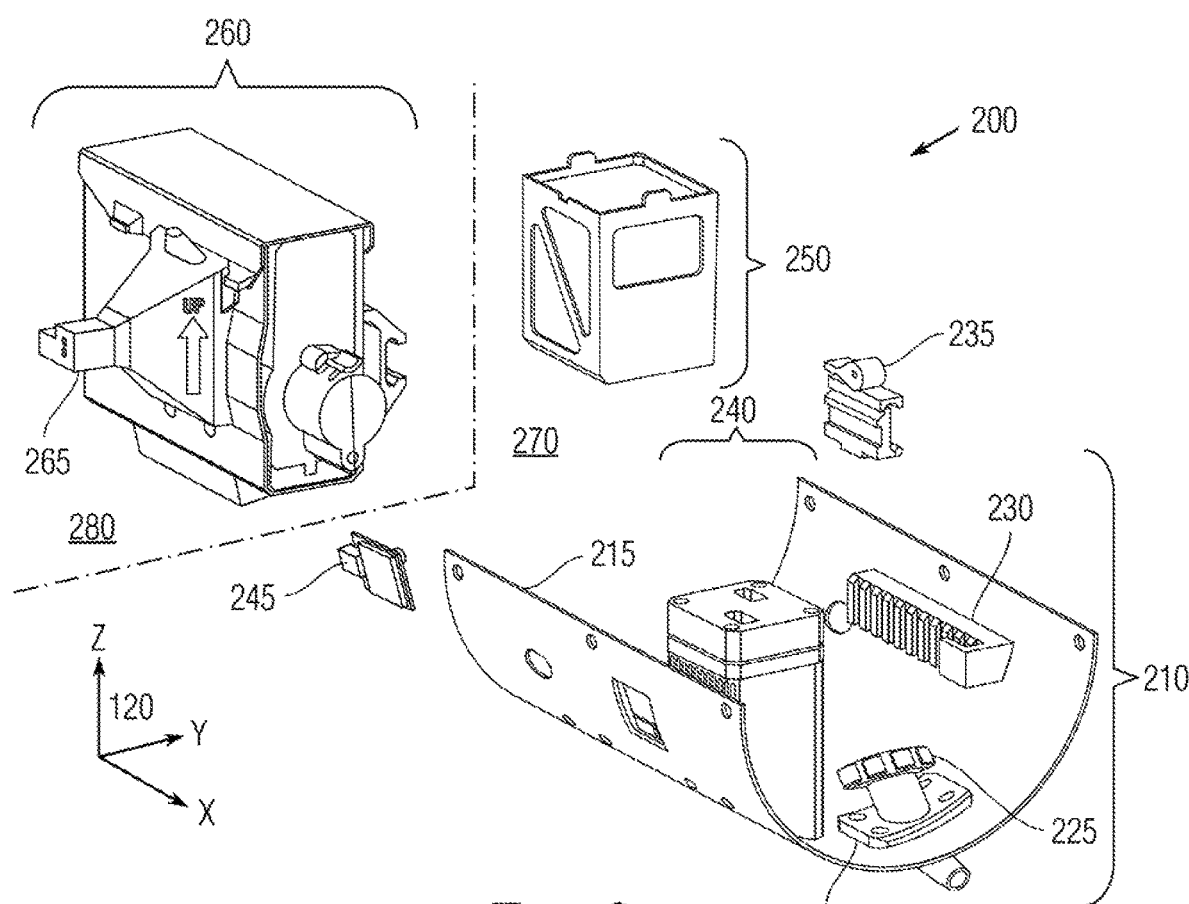
FIG. 2 is an isometric view of a chemical sensor payload package.

FIG. 2 presents an isometric exploded view 200 of components for an exemplary chemical sensor package for insertion into the interface 130. A housing 210 includes a half-cylinder shell 215. An air intake (or scoop) 220 with a threaded seal 225 mounts on the shell 215 towards the front end. A Picatinny rail mount 230 attaches to the port side of the shell 215. A removable rail clamp 235 attaches to the mount 230. A communications module 240 is disposed in the shell 215 towards the front starboard side, and connects to a GPS patch antenna 245. A battery module 250 provides electrical power to the sensor package. A detector sensor assembly 260, including a camera 265, attaches to the mount 230 and the shell 215. The components can be categorized by an interface portion 270 and a mission module portion 280.

Figure 3A:
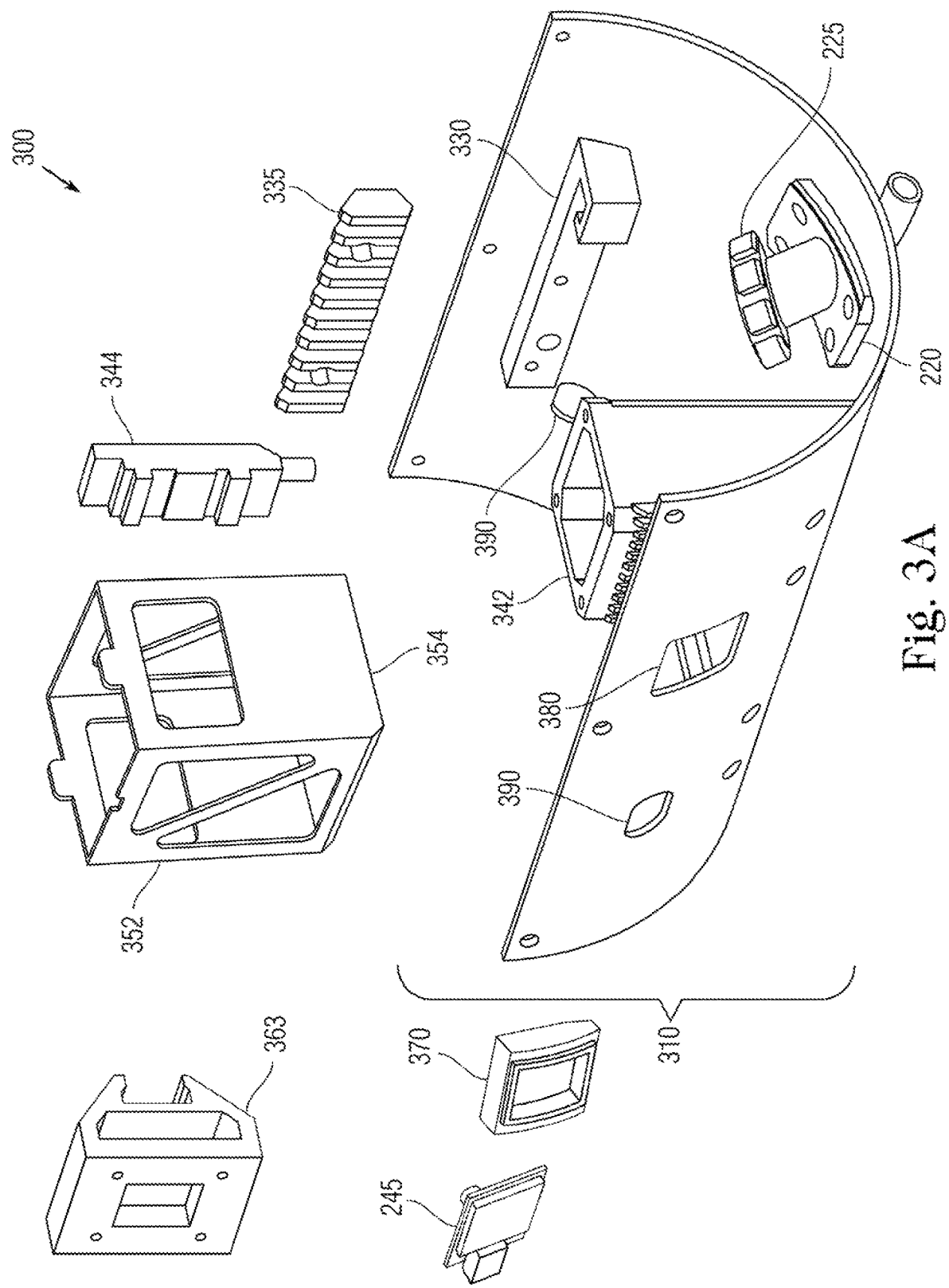
Figure 3C:
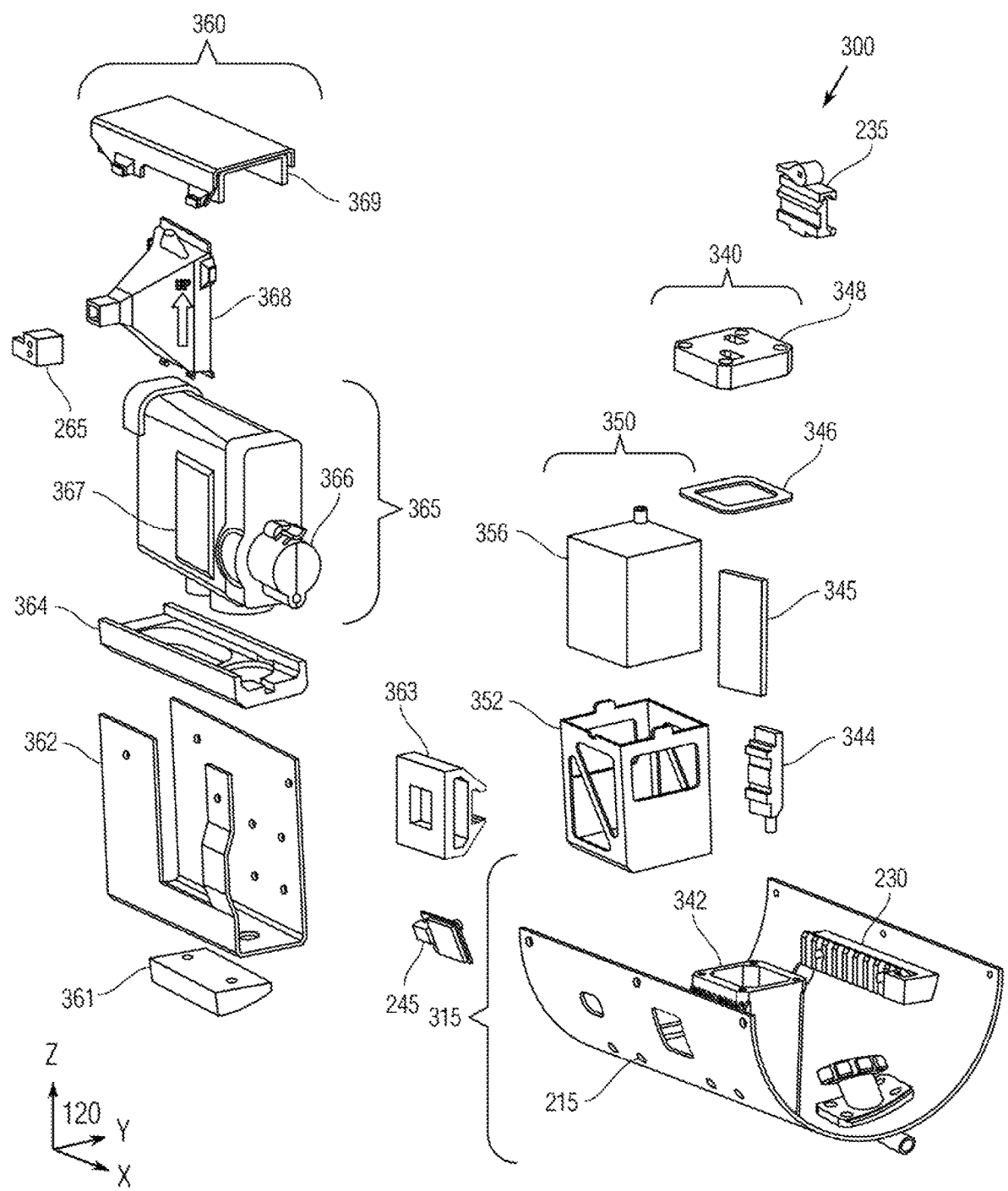

FIGS. 3A, 3B, 3C and 3D illustrate isometric exploded views 300 of components for the chemical sensor package. In particular, FIG. 3A provides details of the interface portion 270, while FIGS. 3B and 3C additionally feature mission module components 280. The mount 230 includes a clevis 330 that attaches to the shell 215 and a rail 335 that connects to the clevis 330. The communications module 240 comprises communications components 340 that include a communications box 342, a transceiver 344, on-screen display (OSD) chip 345, gasket 346 and cover 348. The battery module 250 comprises battery components 350 that include a battery cage 352 with a lug 354. A battery 356 can be inserted into the cage 352 to supply direct current (DC) electric power.

Figure 3D:
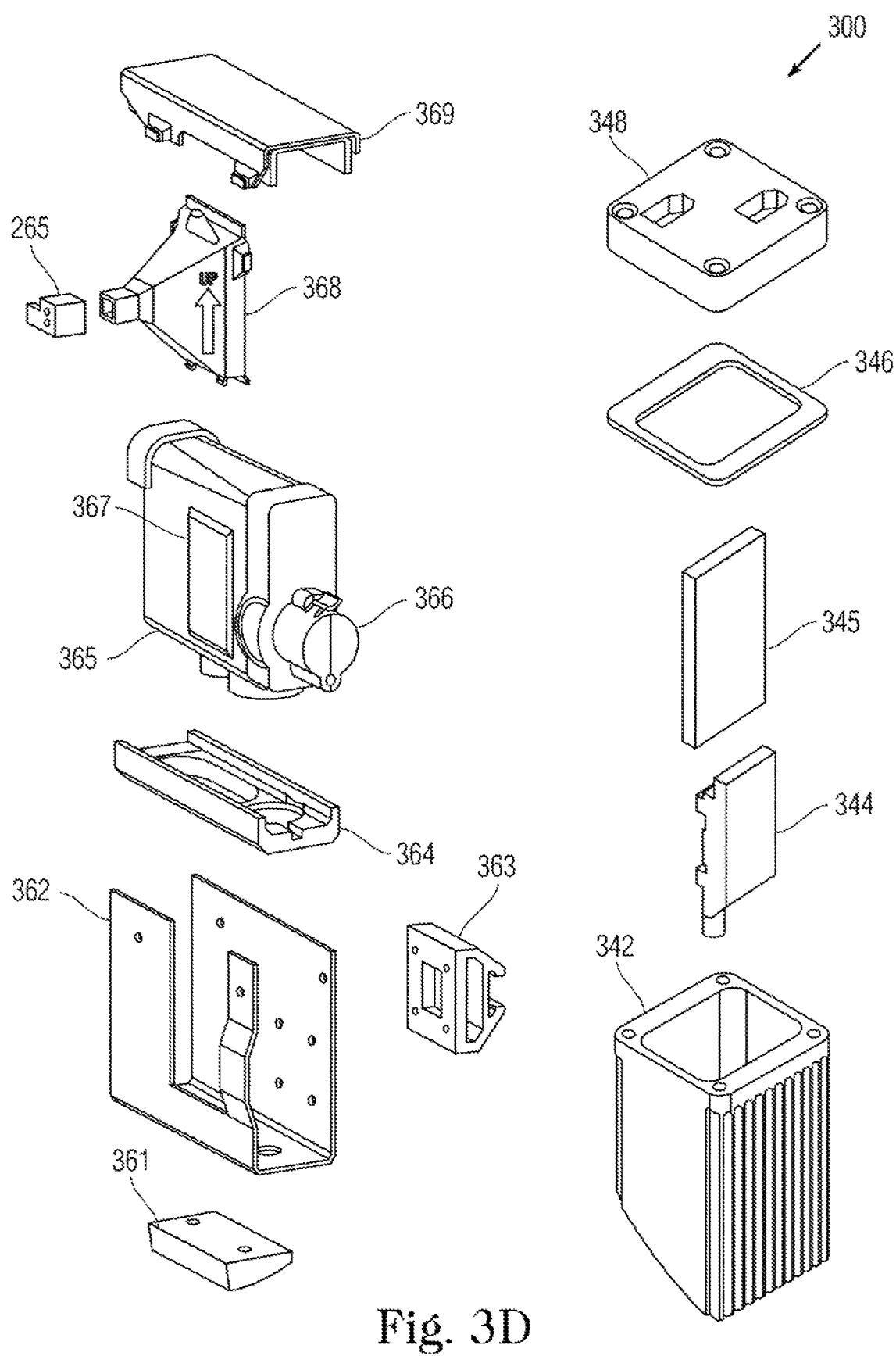

The detector assembly 260 comprises module components 360 that include a shell-facing spacer 361, an interface box 362, a box rail interface 363, a module spacer 364, a joint chemical agent detector (JCAD) 366 with a display screen 367, a camera frame 368 with the camera 265 and a module clip 369. The GPS antenna 245 for the interface portion 270 can be secured by an antenna housing 370 for insertion into orifice 380. The shell 215 includes additional orifices 390 for the exhaust of sampled air. FIG. 3D illustrates additional exploded views 300 of components for the detector assembly 260 and the communications module 240.

Figure 4A:
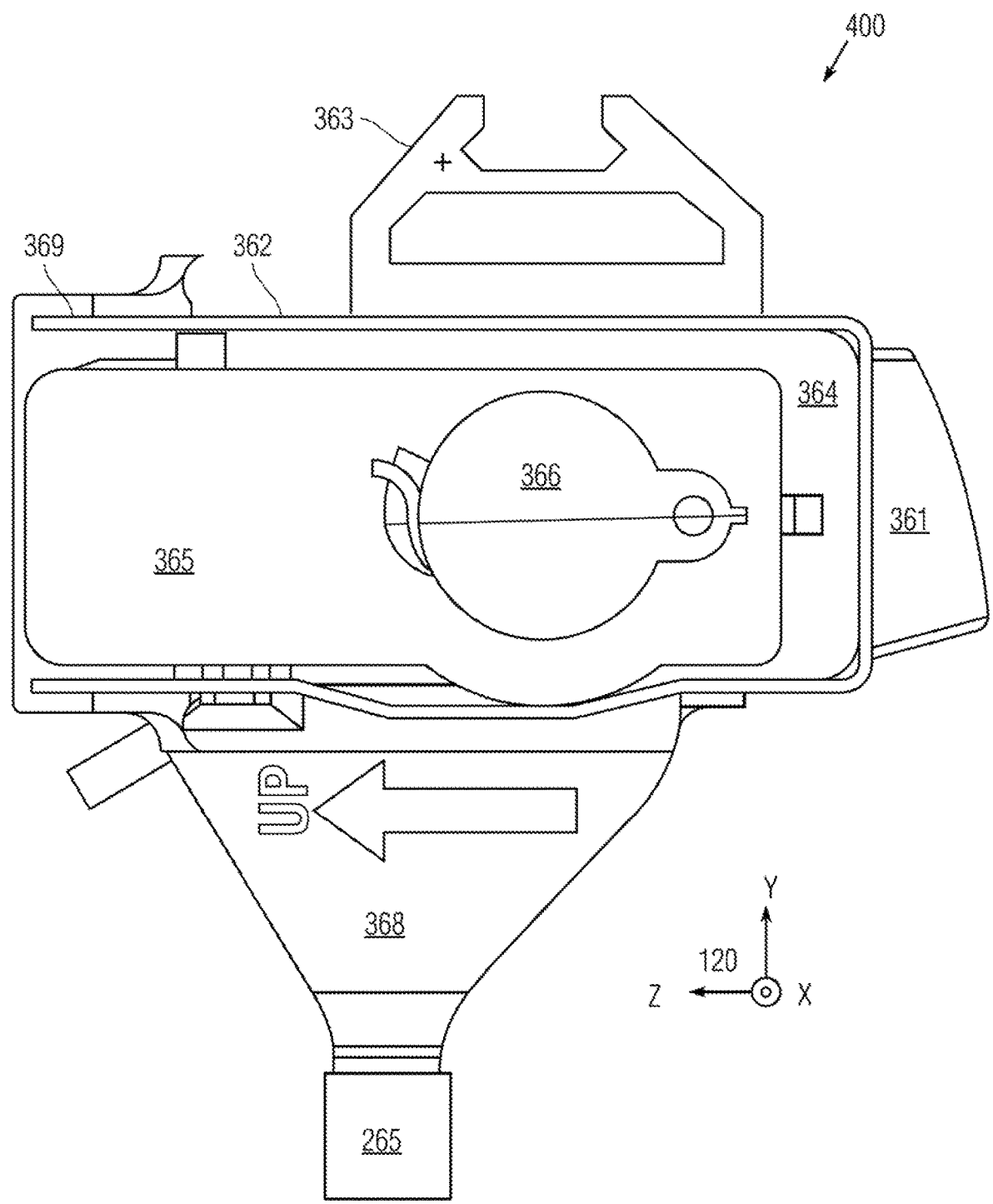
FIGS. 4A, 4B and 4C and 4D are respective isometric, plan and elevation views of a chemical sensor assembly.
Figure 4B:
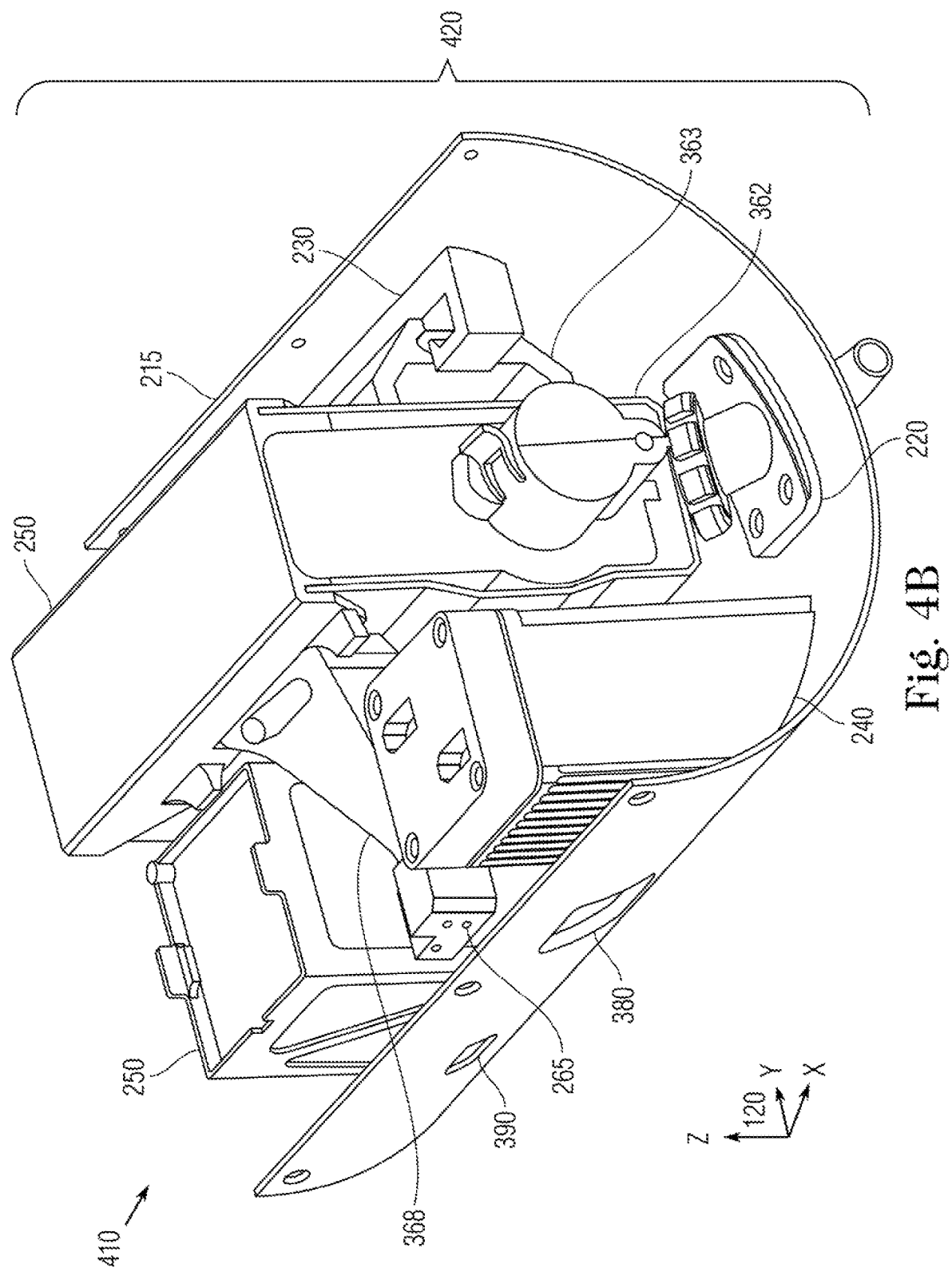
Figure 4C:
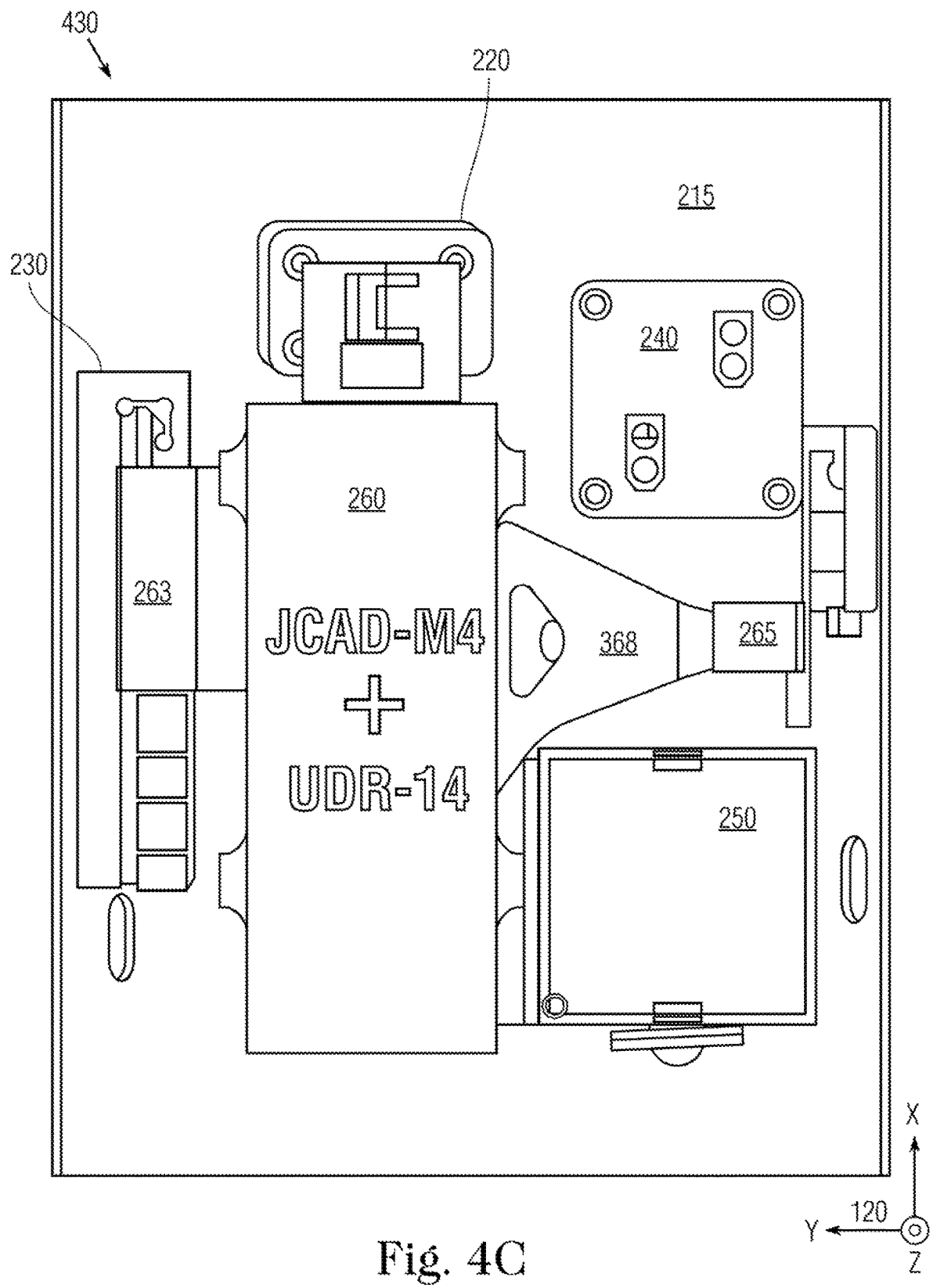
Figure 4D:
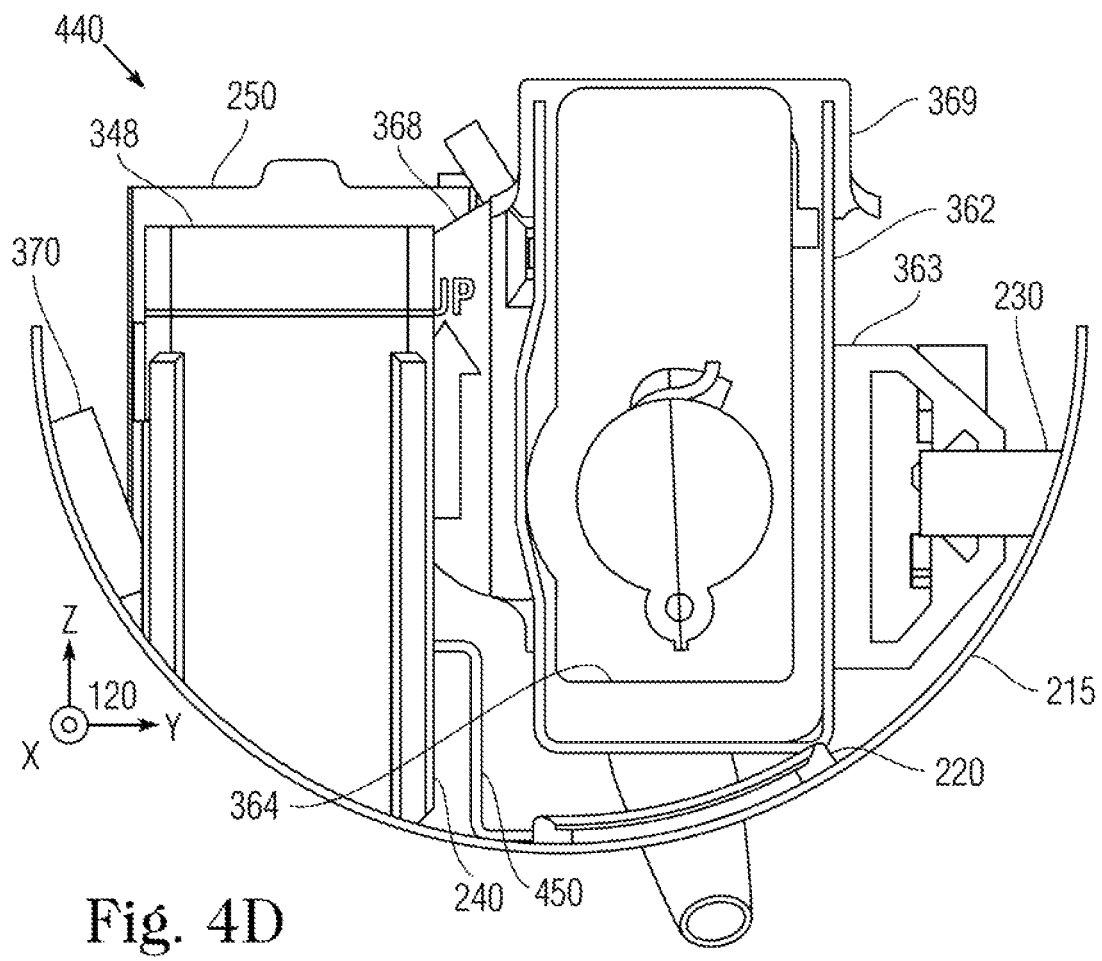

FIG. 4A shows an elevation assembly view 400 facing aft of a chemical package assembly 410. FIG. 4B illustrates an isometric assembly view 420 of the assembly 410 installed on the shell 215 including components for the interface section 270 and the mission module 280. The JCAD 366 includes a display screen 367 for providing imagery to be photographed by the camera 265. FIG. 4C features a plan assembly view 430 of the chemical package assembly 420 in the shell 215, while FIG. 4D provides an elevation assembly view 440 of the chemical package assembly 420 including a battery bracket 450 for securing the battery module 250 within the interface section 270.

Figure 5A:
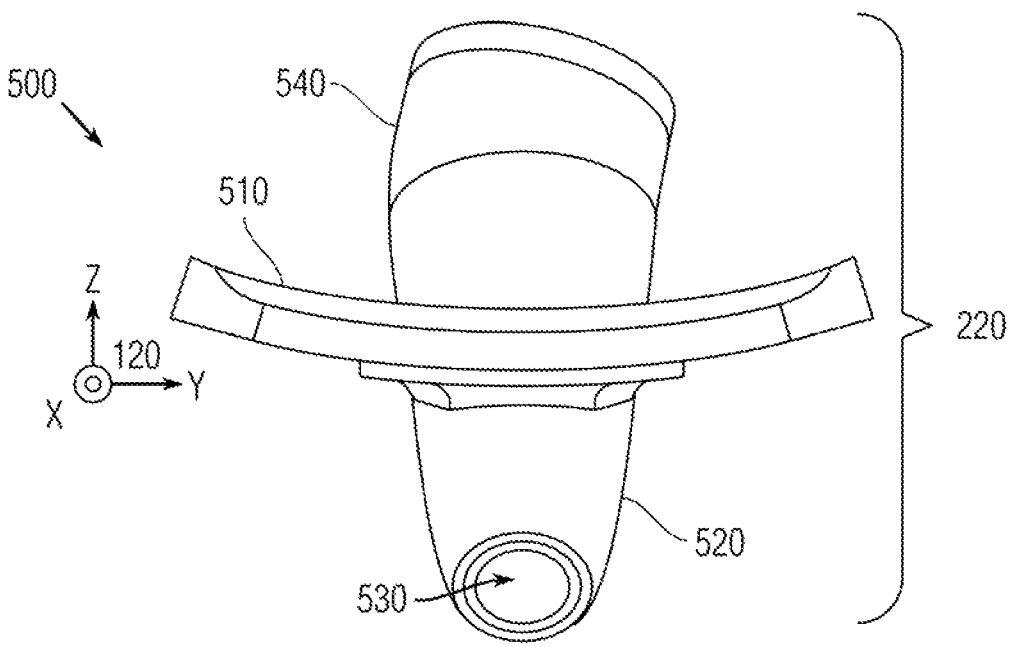
FIGS. 5A, 5B and 5C are respective elevation and plan views of an air intake.
Figures 5B, 5C:
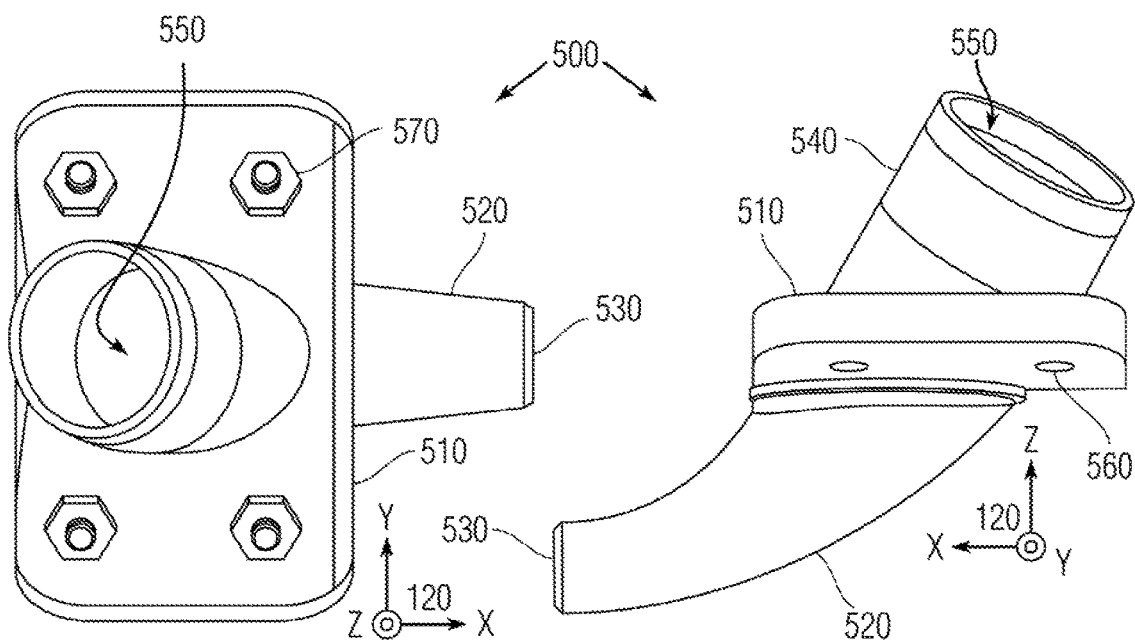

FIGS. 5A, 5B and 5C show respective elevation, plan and elevation views 500 of the air intake 220. FIG. 5A features the air intake 220 facing aft, revealing a mounting flange 510, an entrance nozzle 520 with its intake port 530, and an exit diffuser 540. FIG. 5B shows the air intake 220 from above, including the exhaust port 550. The flange 510 includes a set of through-holes 560 for mounting to the shell 510 by removable fasteners 570, such as nuts and bolts.

Figures 6A, 6B:
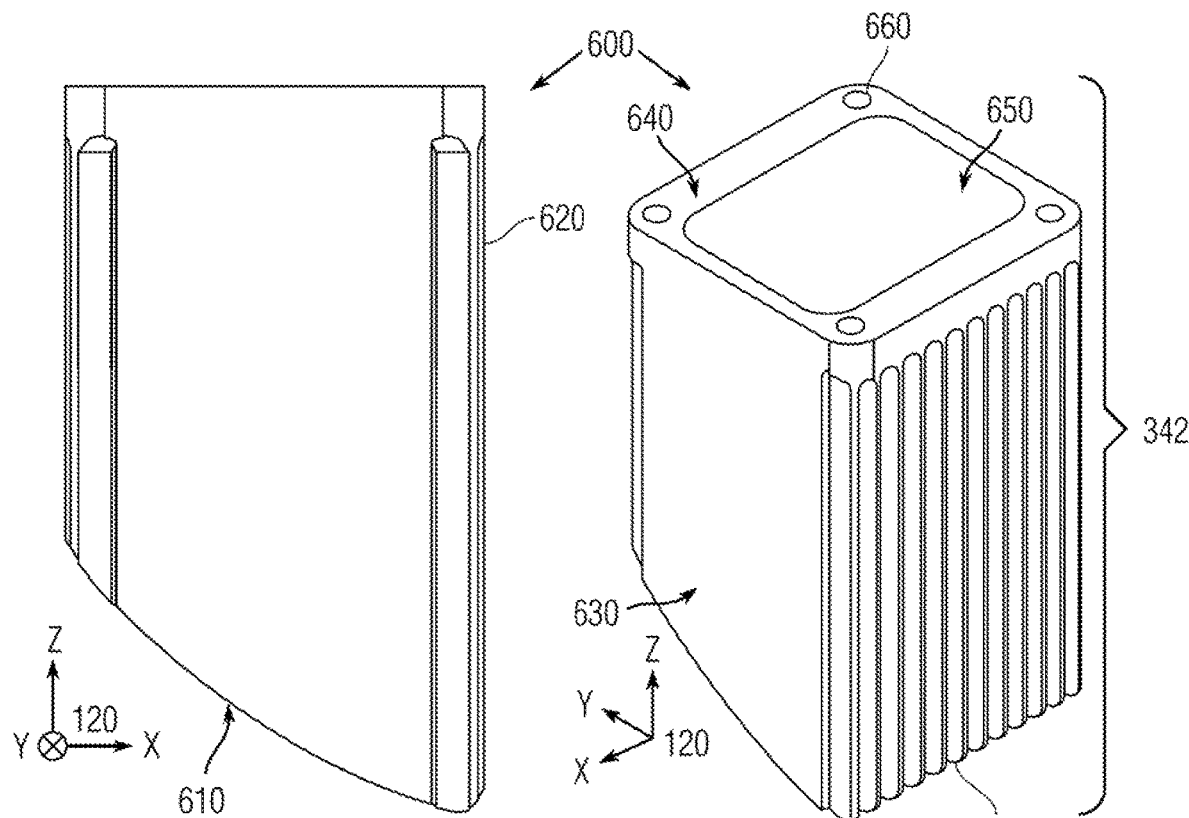
FIGS. 6A and 6B are respective elevation and isometric views of a communications box.

FIGS. 6A and 6B show elevation and isometric views 600 of the communication box 342. A bottom surface 610 mounts to the shell 215, a long corrugated surface 620 faces starboard (with a short corrugated surface facing port) and a flat surface 630 faces forward. The top surface 640 includes an opening 650 for insertion of the transceiver 344 and OSD chip 345, as well as mounting holes 660 enable fasteners to be inserted through the gasket 346 and the cover 348 for assembly of the communications module 260.

Figure 7A:
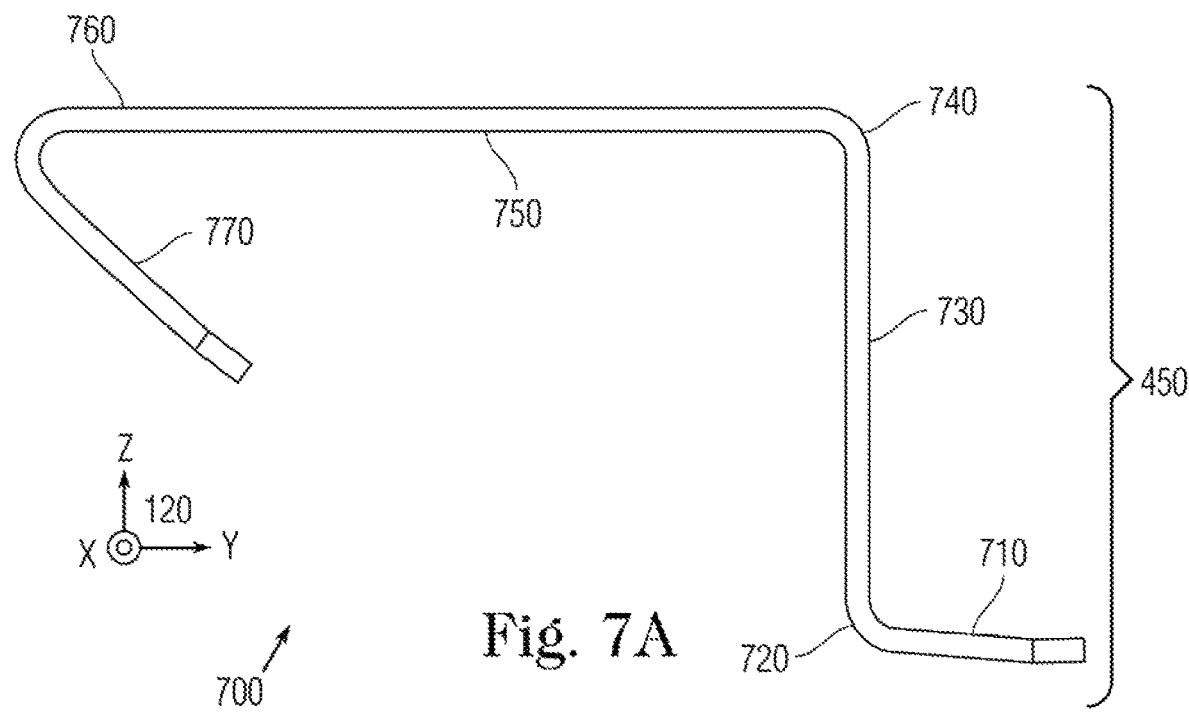
FIGS. 7A and 7B are respective elevation and plan views of a battery bracket.
Figure 7B:
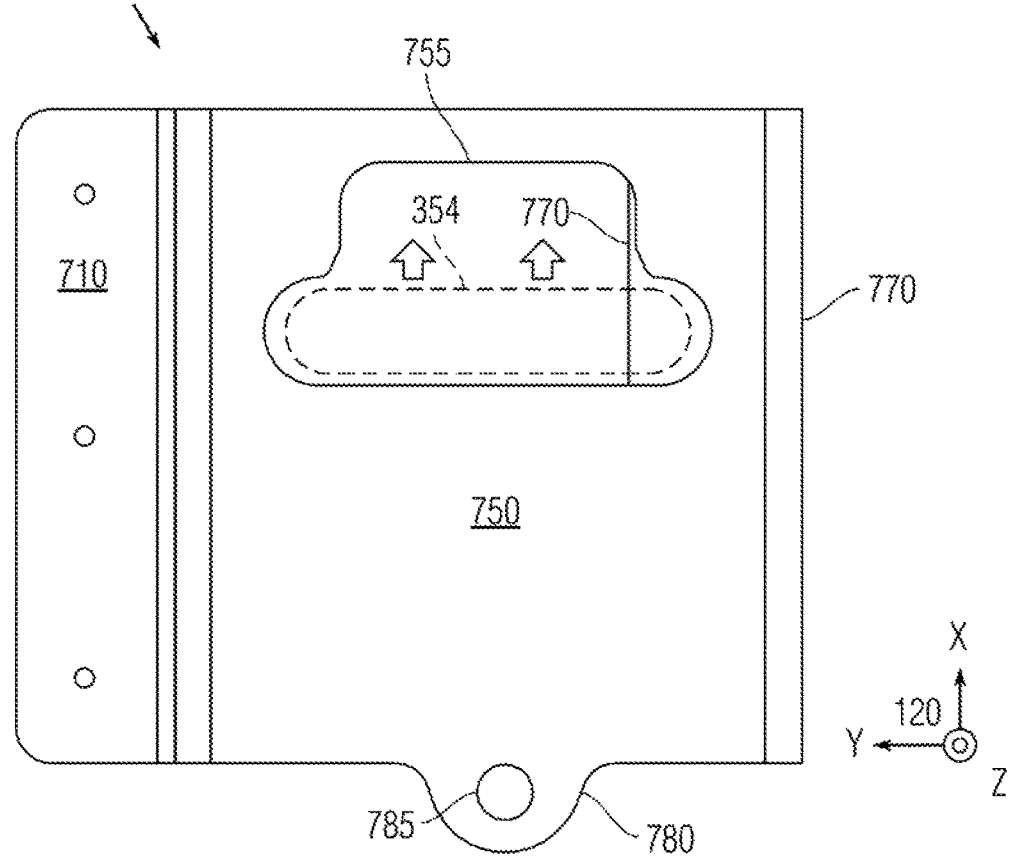

FIGS. 7A and 7B show elevation and plan views 700 of the battery bracket 450 that attaches to the shell 215. A bottom interface flange 710 mounts to the shell 215 interior. A first bend 720 connects the flange 710 to a vertical brace 730. A second bend 740 connects the brace 730 to a mounting plate 750 having an open socket 755. A third bend 760 connects the plate 750 to a support flange 770. The socket 755 receives the lug 354 of the battery housing 352. The plate 750 includes an extension 780 with a bolt hole 785 for receiving a cotter pin that secures the battery cage 352 to the battery bracket 450.

Figure 8A:
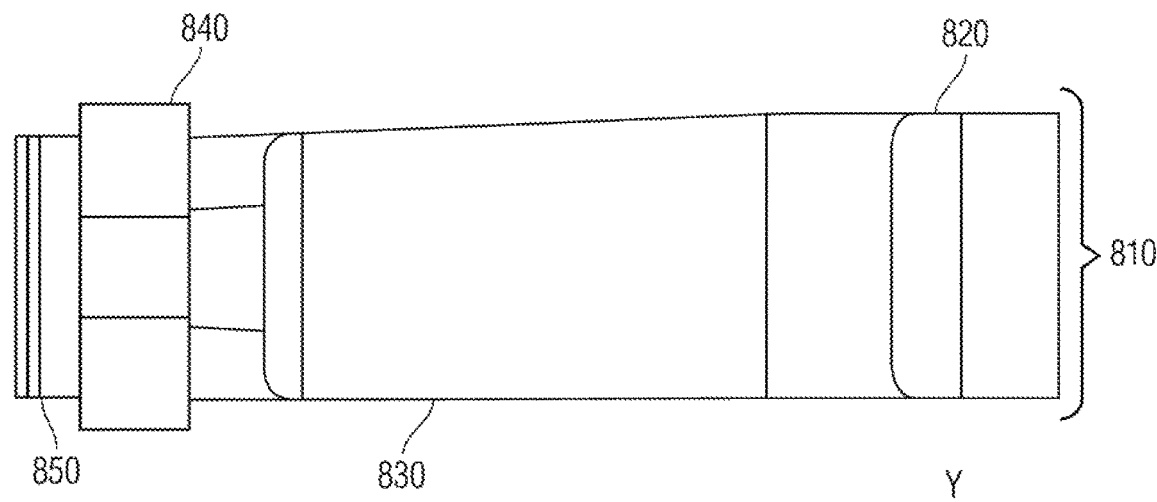
FIGS. 8A and 8B are elevation and plan views of an AN-UDR-14 radiological sensor housing.
Figure 8B:
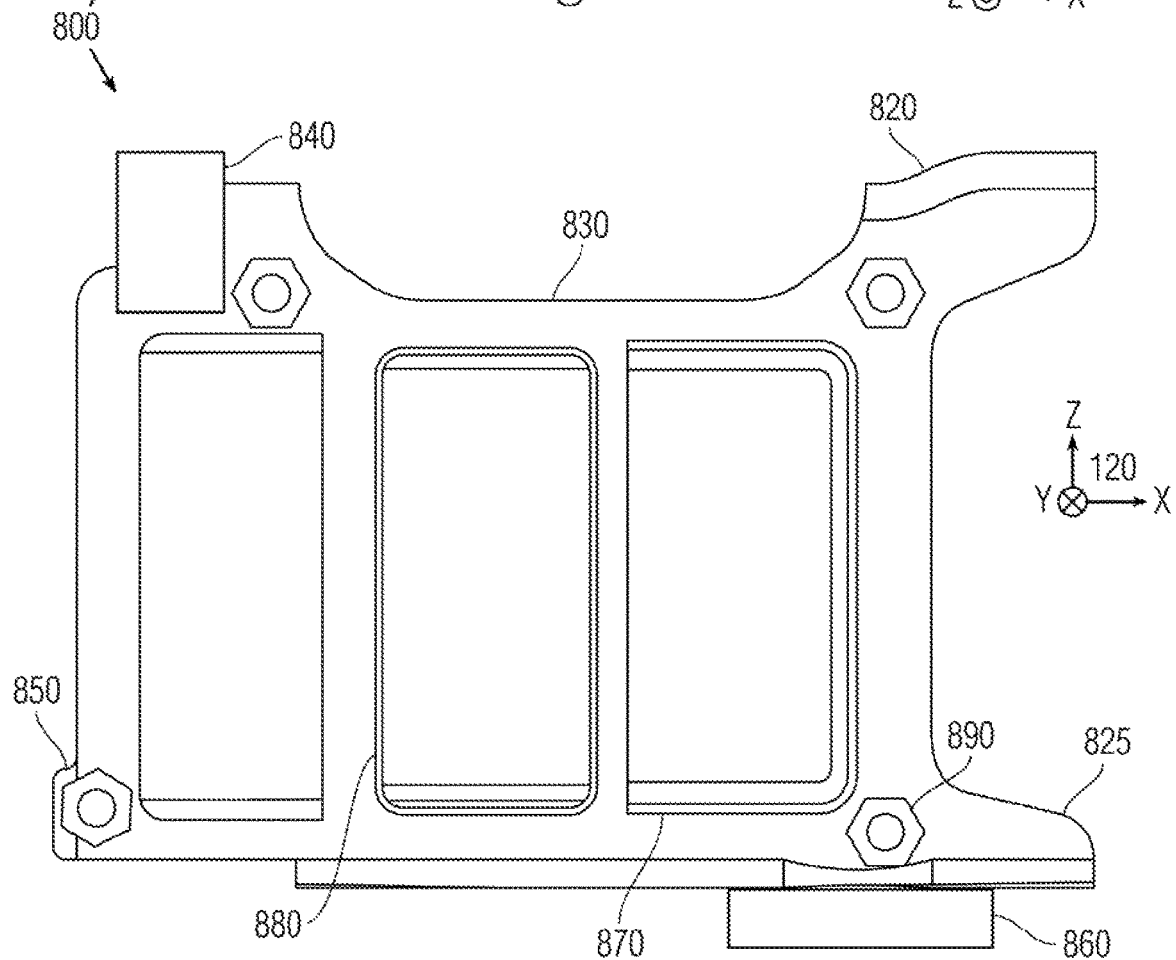

FIGS. 8A and 8B show respective plan and elevation views 800 of a radiological sensor housing 810 for an AN/UDR-14 hand-held sensor from Tradeways LTD, Annapolis, Md. An upper fore corner 820 and lower fore corner 825 extend beyond a central cage 830 to protect the AN/UDR-14 sensor (not shown) inside. An upper rounded flange 840 and a rear bumper 850 also provide additional protection. A rounded foot 860 extends below the housing 810 that includes windows 870 and 880 for controls access of the AN/UDR-14 sensor. The sensor housing 810 can be composed of two bilaterally separate portions fastened together by sets 890 of nuts and bolts.

Figure 9A:
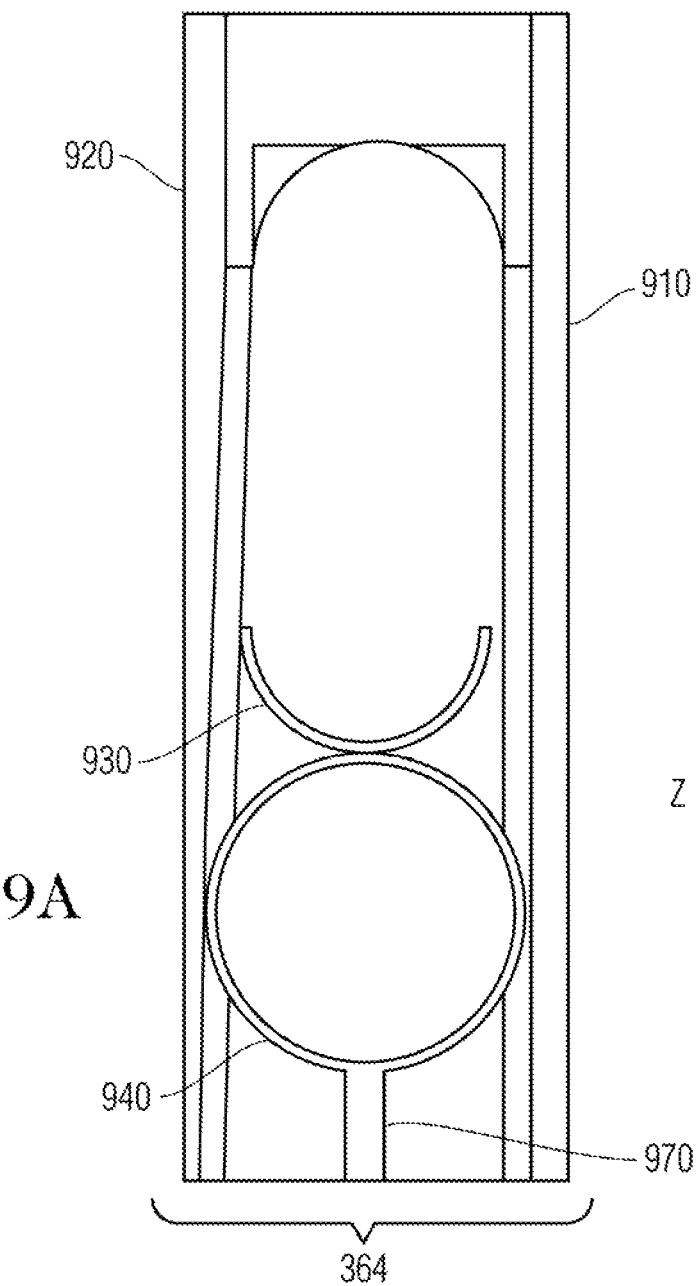
FIGS. 9A and 9B are elevation and plan views of a module spacer.
Figure 9B:
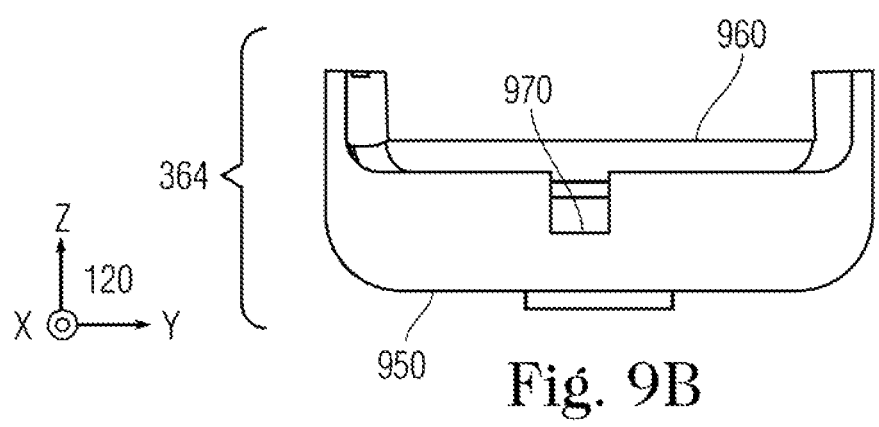
Figure 10A:
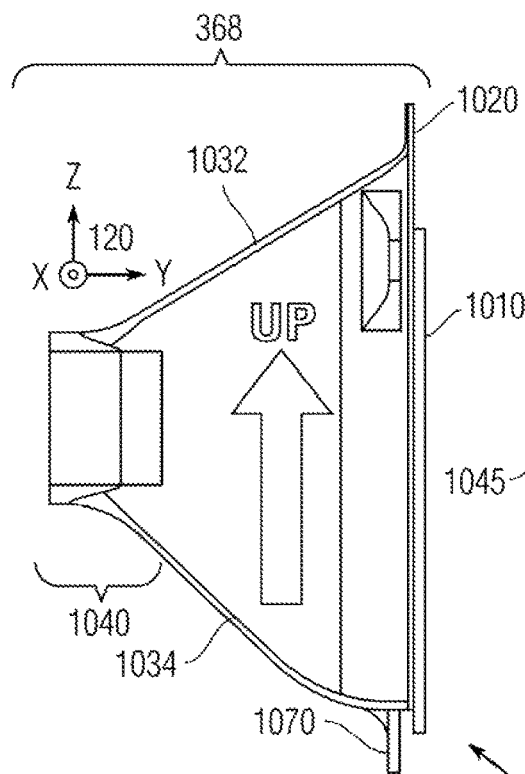
FIGS. 10A, 10B, 10C and 10D are elevation and plan views of a camera mount.
Figure 10B:
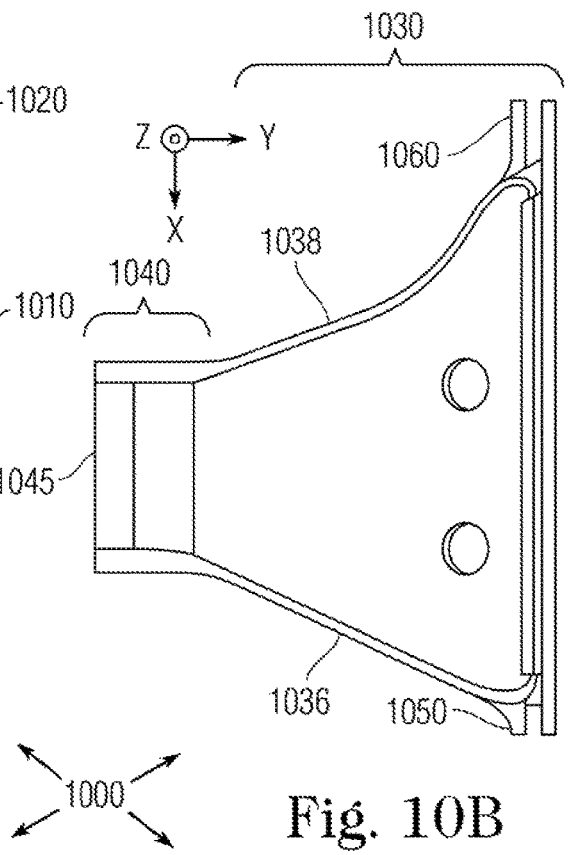
Figure 10C:
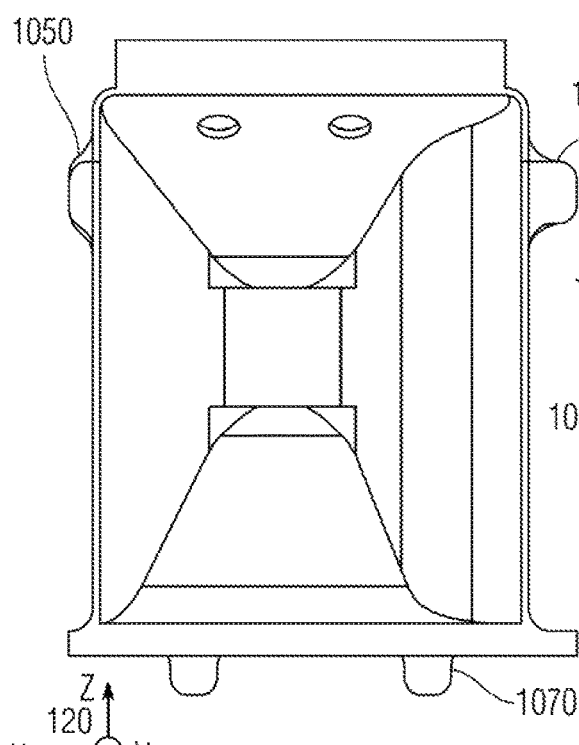
Figure 10D:
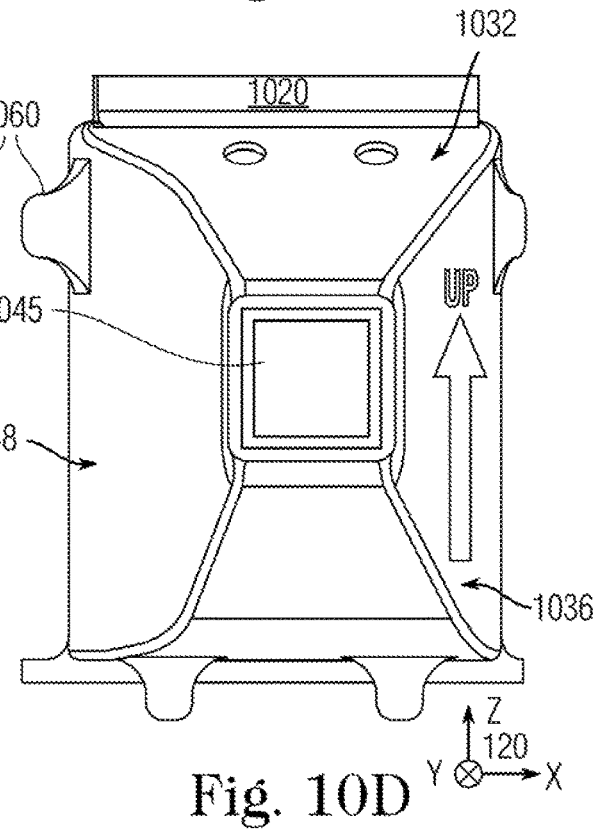

FIGS. 9A and 9B show elevation and plan views 900 of the module spacer 364, including port and starboard sides 910 and 920. A mid spacer 930 enables insertion of the JCAD sensor 366 or radiological sensor housing 365 for an AN/UDR-14. A rounded orifice 940 receives the foot 860 of the housing 365. A bottom surface 950 engages the interface box 352, while an internal top surface 960 marks the levels from which the orifice 940 descends. A notch groove 970 extends forward from the orifice 940.

FIGS. 10A, 10B, 10C and 10D show elevation and plan views 1000 of the camera frame 268. A port face 1010 abuts against the display screen 367 of the JCAD sensor 366. An upper port flange 1020 interfaces with the sensor housing 365. A field-of-view cowl 1030 features narrowing sides, including upper 1032, lower 1034, fore 1036 and aft 1038. A starboard segment 1040 provides an opening 1045 for mounting the camera 265. Tabs at the corners 1050, aft 1060 and starboard 1070 enable alignment of the frame 268 with other mission module components 280.

The camera frame 268 was designed to accomplish two objectives: First, to create and a controlled environment by the cowl 1030 to attenuate ambient light for restriction to a specific level and direction for avoiding sensor screen glare in the video feed of the display screen 367. Second, to maintain a steady, constant distance from the focal plane at the display screen 367, to mitigate the UAV's in-flight vibration from affecting the video quality, accomplished by mounted the camera 265 to the display screen 367, so they move together.

Figure 11A:
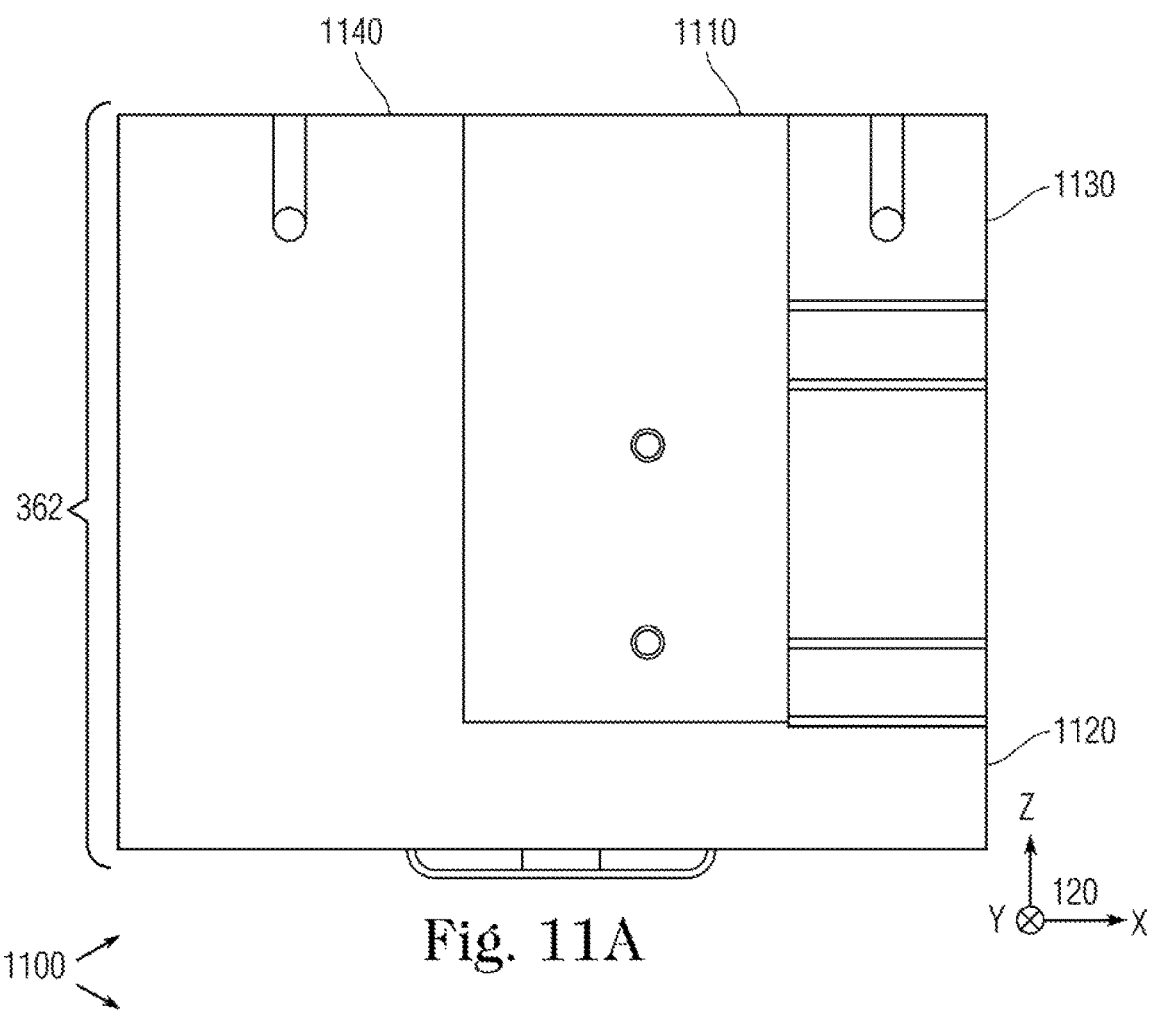
FIGS. 11A and 11B are elevation views of an interface box.
Figure 11B:
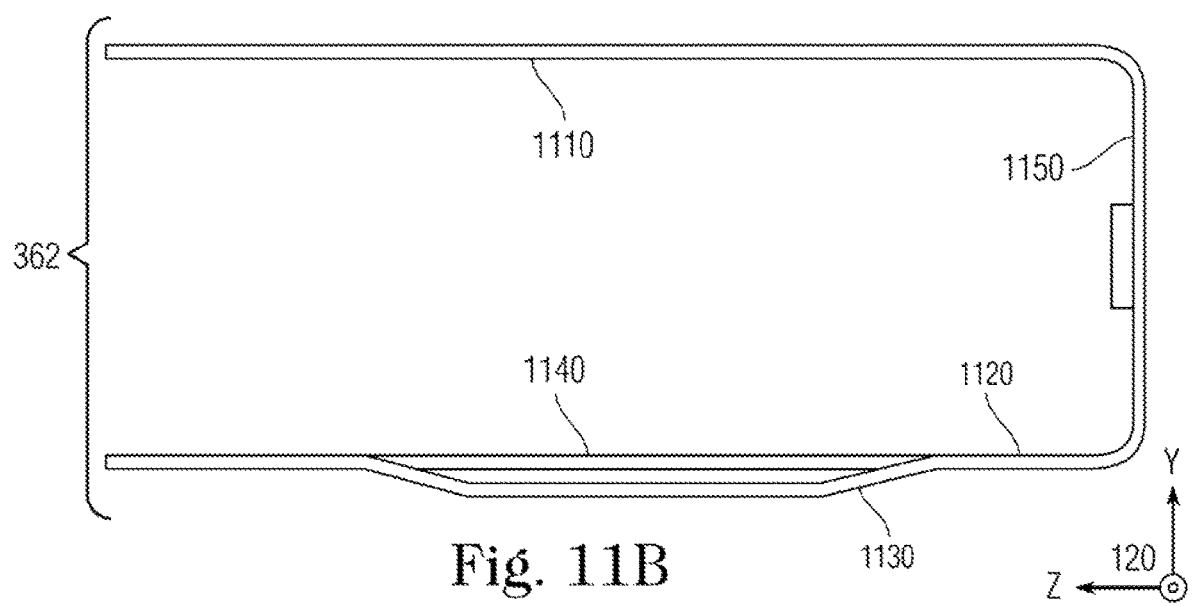

FIGS. 11A and 11B show elevation and plan views 1100 of the interface box 362. A port wall 1110 flanked by a starboard base 1120 bound the spacer 364 and housing 365. Fore and aft flanges 1130 and 1140 extend upward from the base 1120 to secure the housing 365. A bottom bridge 1150 connects the wall 1110 and base 1120 together as a surface to receive the bottom of spacer 950.

Figure 12A:
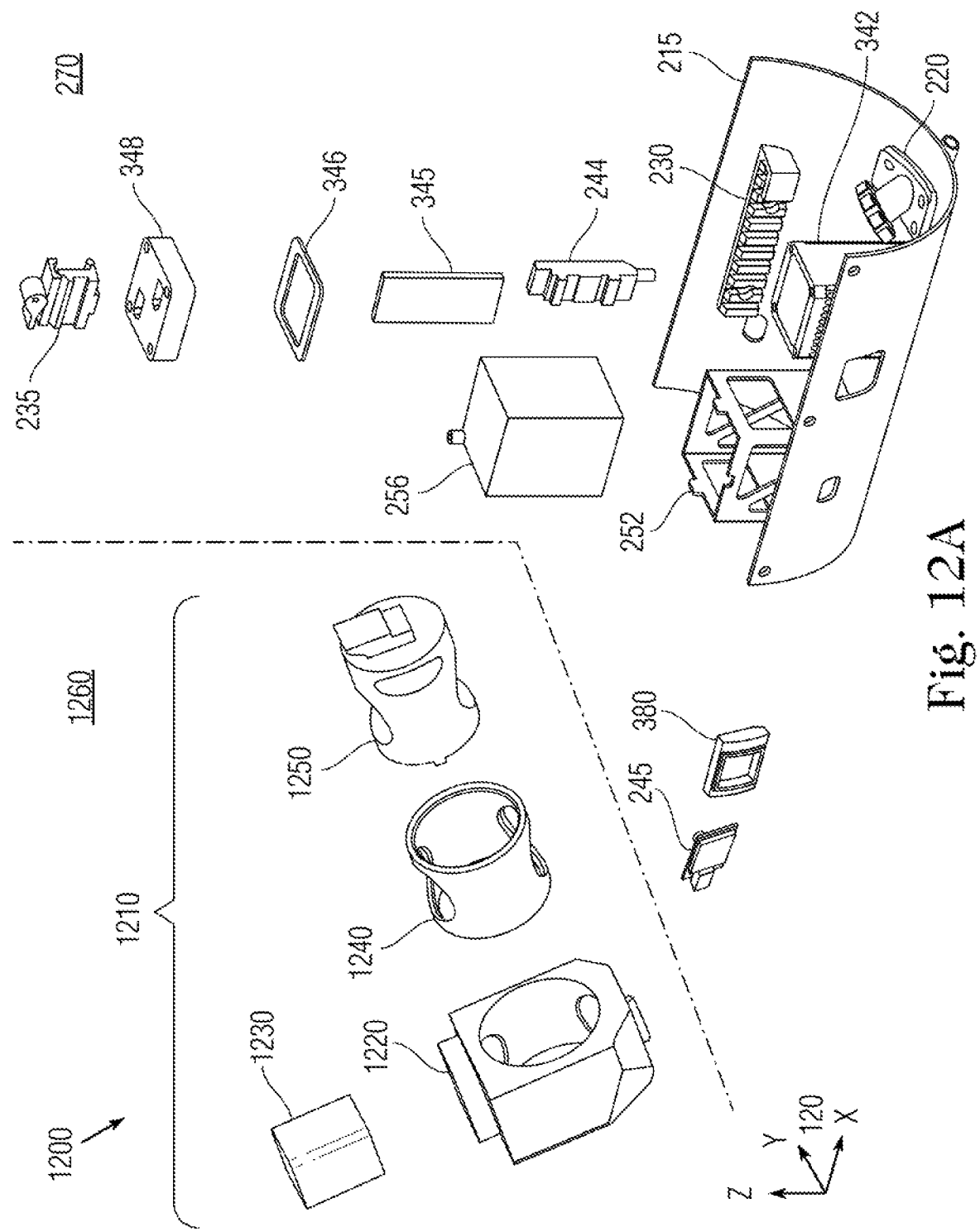
FIGS. 12A and 12B are isometric exploded views of components for the interface section and biological mission module components.
Figure 12B:
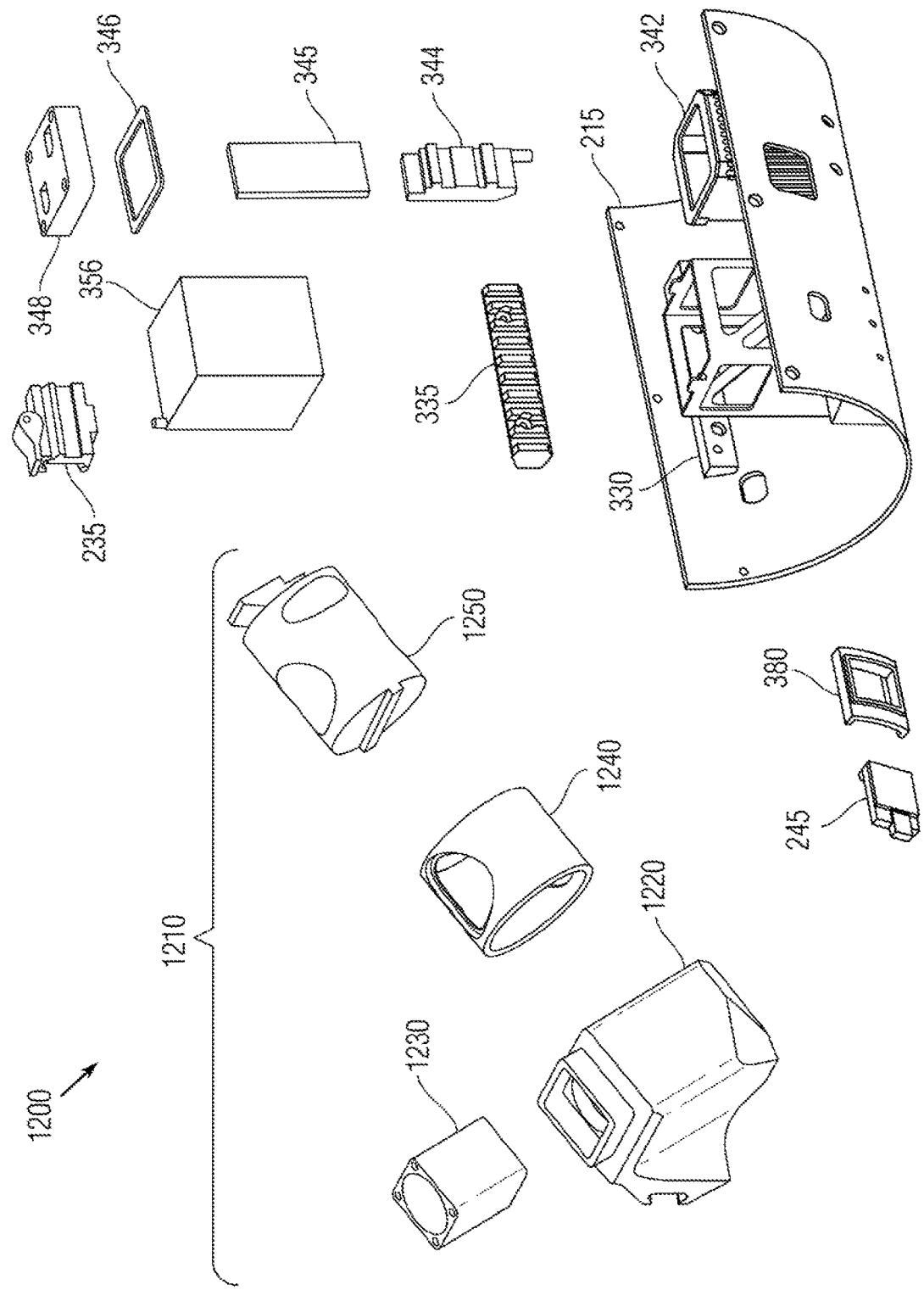

FIGS. 12A and 12B show isometric exploded views 1200 of biological collection components 1210 for a separate configuration as another embodiment. These include a module housing 1220 with an auxiliary commercial off-the-shelf (COTS) fan 1230, a cartridge gasket 1240 and a COTS Dry Filter Unit (DFU) cartridge 1250. The interface module components 270 are the same as in the chemical detection configuration, and distinguished from the biological threat detection module 1260.

Figure 13:
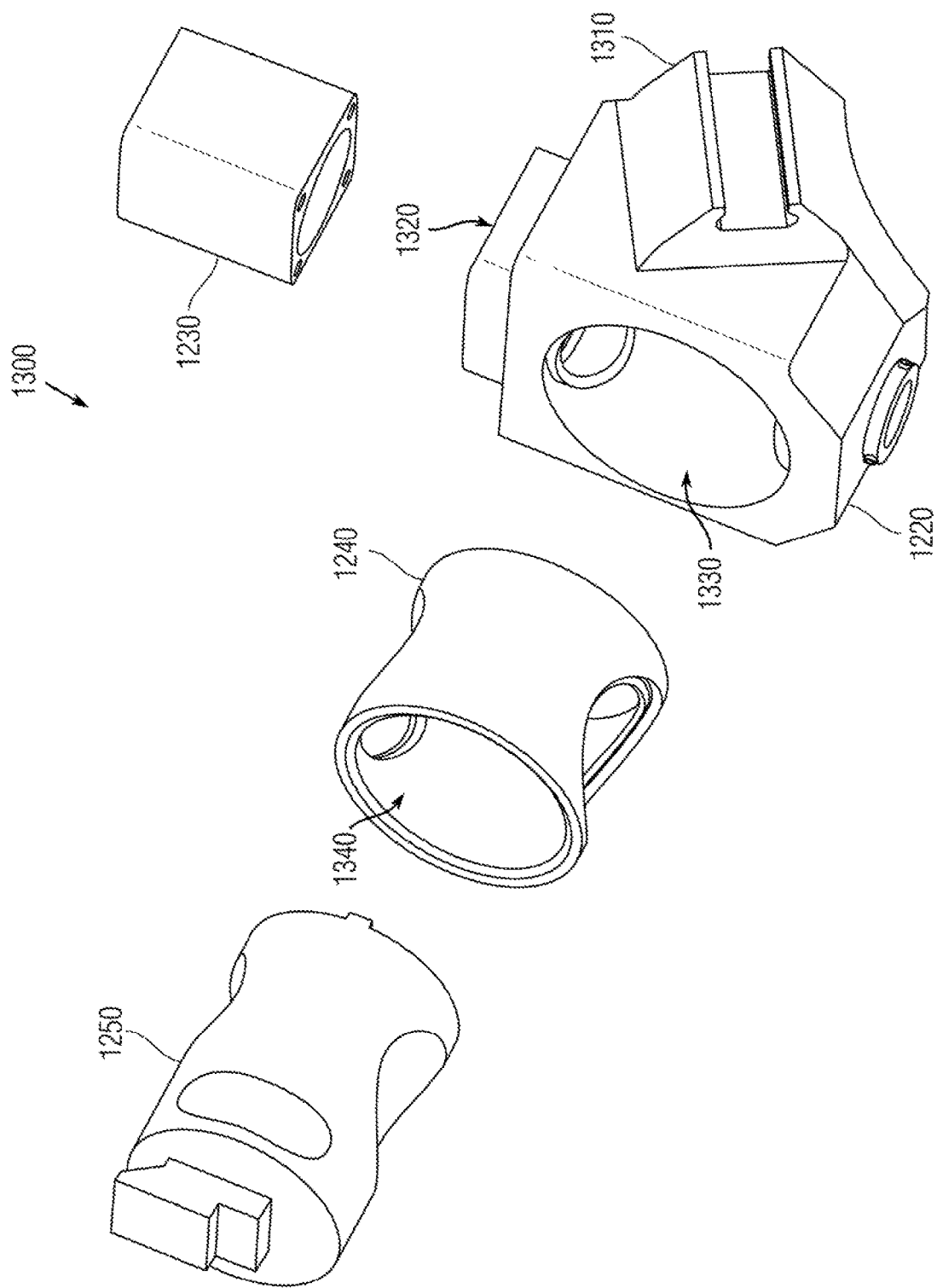
FIG. 13 is an isometric view of biological collector components.

FIG. 13 shows an isometric exploded view 1300 of the biological detection components. The housing 1220 includes an integral slide interface 1310 analogous to the rail interface 363, as well as several openings 1320 and 1330. The fan 1230 inserts into the first opening 1320. The gasket 1240 inserts into the second opening 1330. The DFU cartridge 1250 inserts into a third opening 1340 of the gasket 1240.

Figure 14A:
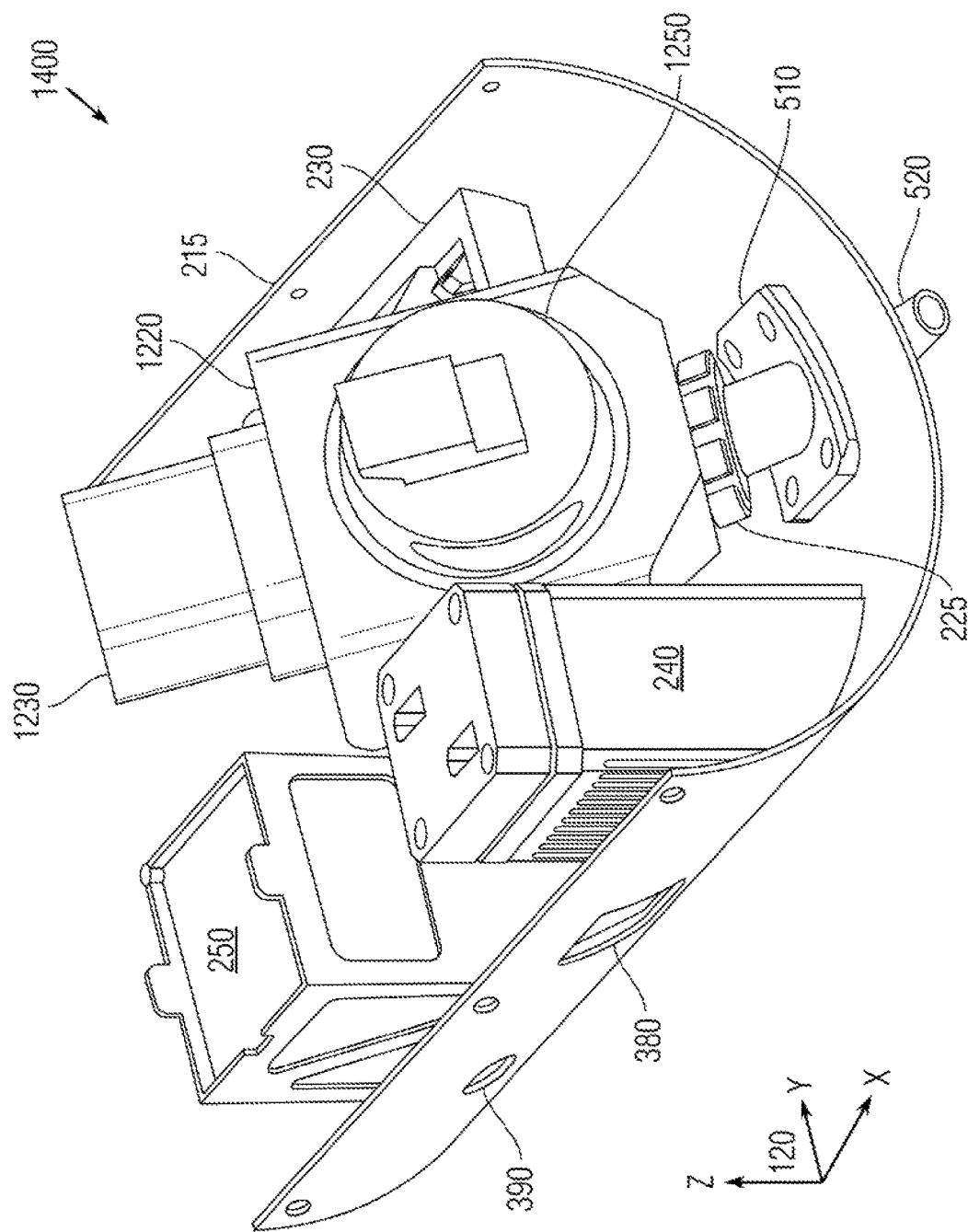
FIGS. 14A and 14B are isometric and plan views of a biological collection payload package.
Figure 14B:
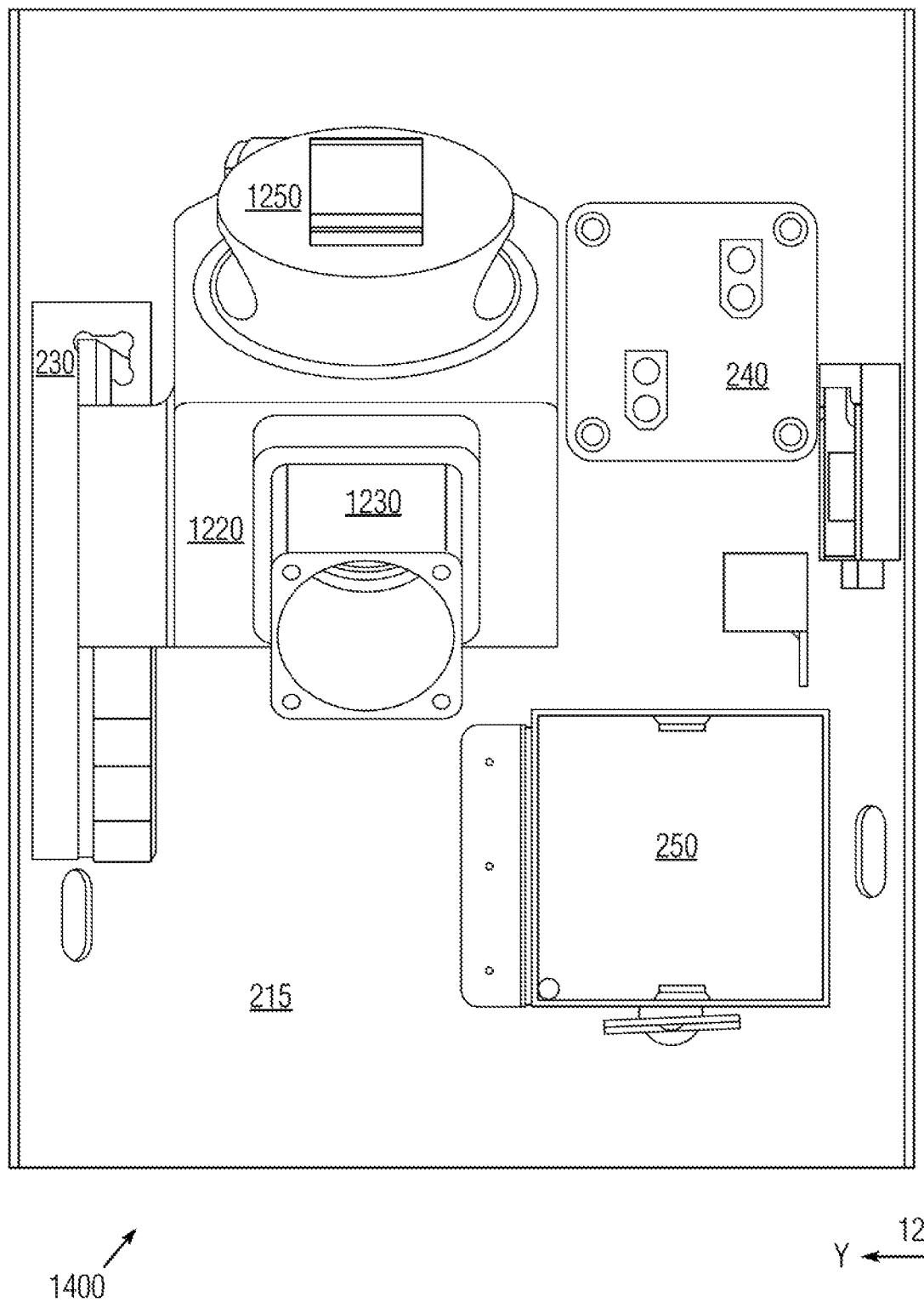

FIGS. 14A and 14B show isometric and plan assembly views 1400 of biological collection package. The seal 225 attaches the air intake 220 to the housing 1220, with the remaining components including the cartridge 1250 sloping aft. The installed interface assemblies, including communications module 240 and battery 250 are shown adjacent to the biological module collection components.

The key difference between the chemical and biological modules is the extent of their functionality. They both interface with currently fielded sampling devices, but while collection is the extent of the biological module's ability, the chemical module proceeds to identify a threat agent in that sample, and then transmits the threat data to a ground control receiver. Effectively, an operator launches and recovers the biological module, and only afterwards receives threat data in a day or two. Alternatively, the operator flies the chemical module, and receives threat detection data in real time throughout the flight.

Exemplary embodiments include the hemispherical interface shell 215 onto which the subsystems are mounted. The shell 215 was designed to screw into the bottom of the forward payload compartment of the ScanEagle platform 110, but can also integrate with other UAS platforms, including the DJI S1000. In its exemplary manifestation, the shell 215 is formed from an aluminum sheet or plate, and comprises six screw holes to interface with the UAS platform. An on/off switch and patch antenna GPS 245 are affixed to the shell 215. The following subsystems can be integrated with the shell 215, some permanently and some interchangeably, depending on the mission.

The communications box 342 houses the communications electronic components of the interface segment 270, including the OSD chip 345, which overlays the camera feed with GPS data, a transceiver 344, and an antenna 245. The bulk of the antenna 245 is external to the shell 215, and interfaces with the transceiver 344 through the holes 290 and communications box 342. The top of the communications box 348 comprises two built-in power connectors, one for power in from the battery 356 (via a switch integrated into the shell 215) and one for power out. In addition to this, cables from the GPS antenna 280 and camera 265 pass into the communications box 342 through a small gap between the cover 348 and the sealing gasket 346.

In the current Concept of Operations (CONOPS) of the system, the communications box 342 and its contents are affixed to the shell 215 for every mission, and should not be removed in normal operations. In its current manifestation, the communications box 342 is machined from aluminum, and comprises cooling fins on the corrugated surfaces 620 to dissipate thermal energy from the internal electronics. The communications box 342 could be fabricated from another material, including molded or three-dimensional (3D) printed plastics. The communications box, including the lid, was designed entirely in-house using computer aided design (CAD) software.

The battery cage 352 interfaces with a clip 450 that is permanently affixed to the shell 215. The cage 352 includes the bottom lug 354 that inserts into the socket 755 of the clip 450 and pushed aft to lock into position. The cage 352 houses the battery 356 for the interface portion 270, which is currently a COTS 11.1V lithium-ion battery. In its current manifestation, the battery cage 352 is made from digital acrylonitrile butadiene styrene (ABS) plastic and was 3D printed. The cage 352 was designed entirely in-house using CAD software.

The air intake (or scoop) 220 is affixed to the shell 215 via four fasteners 570 in the flange 510, and the entrance nozzle 520 protrudes through a hole in the shell 215. The exit diffuser 540 contain two rings, a smaller inner ring with a rubber gasket, and the larger locking ring 225 around the smaller ring. The rings are used to attach the biological collection module 1260 to the air intake 220. The air intake 220 was designed in-house to meet the requirements of the SCAPEGOAT mission.

The air intake 220 was designed to maintain a steady flow rate at ScanEagle 110 cruising speed, while reducing the velocity of the passing threat cloud to increase chances of detection. Thus, the design of the intake 220, counterintuitively, utilizes a narrow entrance opening 530 that expands cross-section area in the nozzle 520 and diffuser 540, thereby reducing subsonic flow velocity of the sample gas.

While, conventionally, a wide inlet that tapers down would be desired for collecting a maximal amount of chemical or biological warfare agent and concentrating the contents before their introduction to the mission module 280, the development of the SCAPEGOAT system faced a different concern regarding not sample concentration, but rather slowing the air moving from the outside of the aircraft into the intake 220. This was necessary to reduce the pressure experienced by the filter in the biological unit components 1210 in order to prevent rupture, and to ensure that the chemical sensor could thoroughly sample the threat area.

Additionally, maximizing the concentration was not a concern because the CONOPS of the system call for the agent deposited on the filter to be extracted via a buffer solution and analyzed using polymerase chain reaction (PCR), which amplifies the sample, meaning that a minimal amount is needed for confirmatory identification. The current air intake 220 was designed entirely in-house and was 3D printed from a proprietary polymer.

The Picatinny rail mount 230 is a COTS product affixed to the shell 215, and serves as the primary interface between the shell 215 and the mission specific CBR modules. The clevis 330 attaches to the shell 215 using screws and a Picatinny rail 335, designed in-house. The rail mount 230 provides a hard stop for the modules that slide onto the rail 335, ensuring that the operator is able to place them in the correct position consistently. The clevis 330 in its current manifestation is machined out of aluminum. The rail mount 230 also utilizes a COTS clip to fix the modules in place. The Picatinny rail 335 was chosen as an interface for the modules because of its extended use, thus facilitating development of additional modules by external groups.

The assembly for the chemical module 280 was designed in-house. This is used for detection of chemical warfare agents, and utilizes two unmodified COTS chemical sensors: the JCAD M4 and the JCAD M4A1. The chemical mission module 280 comprises the JCAD sensor 366, a clamp interface 363 coupled to the interface box 362, an illuminating camera frame 368, a camera 265, and two clip/insert sets 361 and 369, which are interchanged based on the detector selected.

Of primary concern in designing the chemical module was a desire to incorporate unmodified chemical sensors that are currently fielded to the warfighter. This was done in the interest of minimizing testing/validation of the chemical JCAD sensor 366, which is costly, time consuming, and beyond the scope of Sly Fox Mission 21.

One benefit of the chemical module 280 is that the design can contain either the JCAD M4 or the JCAD M4A1. Each of these JCAD sensor configurations is currently fielded, so the system 360 must be able to accommodate both in order that the assembly 410 could be installed into any UAV, regardless of variant. The box interface 362 is a U-shaped, thin walled enclosure with a cutout in the starboard wall to expose the display screen 367 of the chemical sensor 366 to the camera 265. The camera frame 368 is a quasi-pyramidal shape, the base of which slots into the side of the box interface 362 over the screen, with the camera 265 situated at the apex of the frame 368. The camera 265 for the exemplary configuration is a COTS item originally intended to provide a UAS operator with a first-person view of the aircraft in-flight.

Depending on the JCAD variant selected for flight, one of two clip/insert sets is installed into the interface box 362. Each clip set is shaped to fit the side profile of one JCAD variant, ensuring that the sensor 366 is stable during flight. Additionally, each insert was designed with the appropriate thickness such that the display of sensor is situated in the same place relative to the camera frame 268 regardless of the variant used.

The chemical sensor 366 does not interface directly with the air intake 220, as the biological collection module 1210 does. Rather, the chemical module portion 280 relies on a fumigation method, whereby contaminated air enters the scoop and fills the payload bay, which is vented through exhaust ports 390 so that the air can be constantly refreshed, ensuring that what the sensor 366 detects adequately represents the air outside of the payload compartment. In its current manifestation, the insert 362 is bent aluminum, the housing 365 is formed from 3D printed polycarbonate, the clamp interface 363 is 3D printed ABS, and the camera frame 268 is 3D printed polylactic acid (PLA) plastic.

The radiological detection module utilizes the housing 810 to achieve the same external form function as the JCAD housing 365, thereby utilizing the same mission module assembly 360, including the clamp interface 363, camera 265, and camera frame 368 as well as the same clip set as does the JCAD M4. The radiological unit housing 810 is designed around the AN/UDR-14 device, which is much smaller than either variant (M4 or M4A1) of the JCAD sensor 366, necessitating custom housing for accommodation. The housing 810 subdivides into two halves, which are disposed around the radiological sensor (not shown) and bolted together, leaving the internal electronics safely enclosed but with the buttons and screen exposed. The profile of the housing 365 is functionally identical to that of the JCAD M4, and fits in the same place in the box 362. The housing 810 in its current manifestation was 3D printed from ABS.

The biological collection module 1260 comprises the filter housing 1220, the COTS filter cartridge 1250, and the COTS fan unit 1230. The filter cartridge, which is the same as those used in the Dry Filter Unit (DFU) biological collector 1210, opens into two halves, between which filter media is inserted. The filter housing 1220 interfaces directly with the Picatinny rail 230 on the slide interface 1310, and the filter cartridge 1250 is inserted into the hole 1330 in the housing 1220, which is lined with a gasket 1240 as material to hold the cartridge 1250 in place and to create an airtight seal around the cartridge 1250. The front of the housing 1220 locks onto the air intake 220, using a quarter-turn ring as described in the air intake 220 section.

The fan 1230 pulls air through the air intake 220, which is necessary when the system is fielded on a rotorcraft due to lower forward velocities. Fan power may or may not be necessary when the system is fielded on ScanEagle 110; calculations and assessments show that ram air is sufficient to move biological agents through the scoop and onto the filter.

The system has the potential to be manufactured quickly and cheaply, and most of the system was designed entirely in-house (with the exception of the electronics subsystems). The system could be of interest to any element with an interest in chemical, biological, and radiological defense. Interested parties may be the U.S. Departments of Defense and Homeland Security, including ground forces, Special Forces, Coast Guard, and explosive ordnance disposal (EOD) units; federal, state, and local law enforcement agencies; and corresponding organizations of the allies of the United States.

Exemplary embodiments disclosed have numerous advantages. First is the fact that they utilize unmodified sensors that are currently fielded to U.S. armed forces, rather than novel sensors that must undergo thorough testing and evaluation. Additionally, almost all development was done entirely by the team, meaning that the government retains full ownership over most parts of the system. Lastly, each hardware component was designed to be capable of being manufactured in a variety of techniques, including but not limited to 3D printing, machining, and injection molding.

There is no currently fielded alternative. In designing the system, the team considered alternative technologies to meet the requirement for such a system. Notably, the team considered serial communications between the sensors and the transmitter, rather than reading the screens of the sensors with a camera 265, selected for its flexibility, as it provides a common interface 270 for all of the sensors. This common interface 270 also increases the feasibility of adapting the system to accommodate any future sensors. Another design choice that was made was to pursue biological collection as opposed to biological detection due to the prohibitive size and weight of conventionally available biological detection technologies. Additionally, because there is an incubation period before effects set in, there is more time for post-attack analysis in the event of an attack with a biological warfare agent.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A modular sensor platform for installation on an unmanned aerial vehicle (UAV), said platform comprising:
   an external shell that inserts between sections of the UAV that defines an internal volume;
   an interface module that attaches to said shell within said volume; and a mission module having a structure that attaches to said shell within said volume and contains at least one sensor, wherein said interface module includes a communications package, a battery package and an air intake, and said mission module includes a sensor mount for attaching to said shell, a chemical sensor and a camera to view a display on said chemical sensor.

2. The platform according to claim 1, wherein said mission module further includes a camera frame having first and second interfaces and a cowl disposed therebetween, said first interface attaches to said display on said chemical sensor, said second interface attaches to said camera, and said cowl attenuates ambient light to enable visibility of said display to said camera.

3. A modular sensor platform for installation on an unmanned aerial vehicle (UAV), said platform comprising:

an external shell that inserts between sections of the UAV that defines an internal volume;

an interface module that attaches to said shell within said volume; and a mission module having a structure that attaches to said shell within said volume and contains at least one sensor, wherein said interface module includes a communications package, a battery package and an air intake, and said mission module includes a sensor mount for attaching to said shell, a radiological sensor and a camera to view a display on said radiological sensor.

4. A modular sensor platform for installation on an unmanned aerial vehicle (UAV), said platform comprising:

an external shell that inserts between sections of the UAV that defines an internal volume;

an interface module that attaches to said shell within said volume; and a mission module having a structure that attaches to said shell within said volume and contains at least one sensor, wherein said mission module includes a sensor mount for attaching to said shell, a biological sensor and a camera within a housing to record a display on said biological sensor.

5. A camera frame for attaching a camera to a sensor on a mobile platform, said sensor having a visual display, said frame comprising:

a first interface attaching to the display;

a second interface attaching to the camera; and a cowl for attenuating ambient light to enable visibility of the display, said cowl being disposed between said first and second interfaces.

* * * * *